(12) United States Patent
Coll Crespo et al.

(10) Patent No.: US 9,855,245 B2
(45) Date of Patent: Jan. 2, 2018

(54) METHODS FOR IMPROVING LIPID PROFILES USING ATRASENTAN

(71) Applicant: AbbVie Inc., North Chicago, IL (US)

(72) Inventors: Blas Coll Crespo, Highland Park, IL (US); Dennis Andress, Chicago, IL (US); John J. Brennan, Libertyville, IL (US); James C. Stolzenbach, Buffalo Grove, IL (US)

(73) Assignee: AbbVie Inc., North Chicago, IL (US)

( * ) Notice: Subject to any disclaimer, the term of this patent is extended or adjusted under 35 U.S.C. 154(b) by 24 days.

(21) Appl. No.: 14/888,195

(22) PCT Filed: Apr. 30, 2014

(86) PCT No.: PCT/US2014/036152
§ 371 (c)(1),
(2) Date: Oct. 30, 2015

(87) PCT Pub. No.: WO2014/179453
PCT Pub. Date: Nov. 6, 2014

(65) Prior Publication Data
US 2016/0074363 A1 Mar. 17, 2016

Related U.S. Application Data

(60) Provisional application No. 61/824,199, filed on May 16, 2013, provisional application No. 61/817,645, filed on Apr. 30, 2013.

(51) Int. Cl.
*A61K 31/4025* (2006.01)
*A61K 45/06* (2006.01)

(52) U.S. Cl.
CPC .......... *A61K 31/4025* (2013.01); *A61K 45/06* (2013.01)

(58) Field of Classification Search
CPC ................................................ A61K 31/4025
See application file for complete search history.

(56) References Cited

U.S. PATENT DOCUMENTS

| | | | |
|---|---|---|---|
| 2004/0186083 A1* | 9/2004 | McMahon | A61K 31/56 514/171 |
| 2007/0004745 A1* | 1/2007 | Pickett | A61K 31/522 514/252.17 |
| 2008/0132710 A1 | 6/2008 | Henry et al. | |

FOREIGN PATENT DOCUMENTS

| | | |
|---|---|---|
| WO | 2006034084 A1 | 3/2006 |
| WO | 2006034085 A1 | 3/2006 |
| WO | 2006034094 A1 | 3/2006 |
| WO | 2006034234 A1 | 3/2006 |
| WO | 2009026517 A2 | 2/2009 |
| WO | 2014138738 A1 | 9/2014 |

OTHER PUBLICATIONS

WebMD. "What is Atherosclerosis?" (c) Mar. 5, 2010. Available from: < http://web.archive.org/web/20100305175402/http://www.webmd.com/heart-disease/what-is-atherosclerosis >.*
WebMD. "Statins and Statin Combinations for High Cholesterol." (c) Mar. 27, 2012. Available from: < http://web.archive.org/web/20120327111306/http://www.webmd.com/cholesterol-management/statins-for-high-cholesterol >.*
Raichlin, E., et al. "Efficacy and Safety of Atrasentan in Patients With Cardiovascular Risk and Early Atherosclerosis." Hypertension. (Sep. 2008).*
Gould, P.L. "Salt selection for basic drugs." International Journal of Pharmaceutics. (1986), vol. 33, pp. 201-217.*
Mayo Clinic. "Metabolic syndrome." (c) 2012. Available from: < http://www.mayoclinic.org/diseases-conditions/metabolic-syndrome/home/ovc-20197517?p=1 >.*
Drugs.com. "Statins." (c) Jun. 18, 2012. Available from: < https://www.drugs.com/drug-class/hmg-coa-reductase-inhibitors.html >.*
Barton, M., "Therapeutic potential of endothelin receptor antagonists for chronic proteinuric renal disease in humans," Biochimica et Biophysica Acta, Dec. 2010, vol. 1802, No. 12, pp. 1203-1213.
Best et al., "Coronary Endothelial Function is Preserved with Chronic Endothelin Receptor Antagonism in Experimental Hypercholesterolemia In Vitro," Arteriosclerosis Thrombosis, Vascular Biolology, Nov. 1999, vol. 19, No. 11, pp. 2769-2775.
Bonetti et al., "Endothelin type A receptor antagonism restores myocardial perfusion response to adenosine in experimental hypercholesterolemia," Atherosclerosis, Jun. 2003, vol. 168, No. 2, pp. 367-373.
Kohan et al., Addition of Atrasentan to Renin-Angiotensin System Blockade Reduces Albuminuria in Diabetic Nephropathy, Journal of the American Society of Nephrology, Apr. 2011, vol. 22, No. 4, pp. 763-772.
Reriani et al., "Long-Term Administration of Endothelin Receptor Antagonist Improves Coronary Endothelial Function in Patients With Early Atherosclerosis," CIRCULATION, Sep. 2010, vol. 122, No. 10, pp. 958-966.
International Search Report for Application No. PCT/US2014/036152, dated Aug. 25, 2014, 3 pages.
International Preliminary Report on Patentability for Application No. PCT/US2014/036152, dated Nov. 3, 2015, 8 pages.

* cited by examiner

*Primary Examiner* — Noble Jarrell
*Assistant Examiner* — John S Kenyon

(57) ABSTRACT

The present disclosure is directed to methods for reducing cardiovascular risk in a human subject by administering atrasentan, or a pharmaceutically acceptable salt thereof, in an amount sufficient to effect a reduction of about 5% or more in one or both of (a) total serum cholesterol, relative to the subject's baseline total serum cholesterol, and (b) serum LDL cholesterol, relative to the subject's baseline serum LDL cholesterol.

33 Claims, 13 Drawing Sheets

* $P \leq 0.05$, 0.01 for difference from placebo.

| | Atrasentan 0.75 mg (n = 78) | Atrasentan 0.75 mg (n = 78) | Atrasentan 0.75 mg (n = 78) |
|---|---|---|---|
| Age (years), mean ± SD | 64.3 ± 9.0 | 65.0 ± 9.8 | 64.5 (8.8) |
| Female, n (%) | 10 (20) | 15 (19) | 26 (31) |
| Race, n (%) | | | |
| White | 23 (46) | 36 (46) | 38 (46) |
| Black | 2 (4) | 14 (18) | 13 (16) |
| Asian | 24 (48) | 25 (32) | 28 (34) |
| Other | 1 (2) | 3 (4) | 4 (5) |
| Systolic BP (mm Hg), mean (SD) | 136 (14) | 138 (14) | 136 (15) |
| Diastolic BP (mm Hg), mean (SD) | 72 (10) | 75 (10) | 74 (9) |
| UACR (mg/g creatinine), median | 671 | 878 | 826 |
| Serum creatinine (mg/dL), mean (SD) | 1.5 (0.4) | 1.6 (0.4) | 1.4 (0.4) |
| eGFR (mL/min/1.73 m2), mean (SD) | 49 (13) | 48 (15) | 51 (14) |
| BNP (pg/ml), mean (SD) | 62 (63) | 60 (68) | 46 (41) |
| Statins, n (%) | 38 (76) | 58 (74) | 68 (82) |
| Diuretics, n (%) | 46 (92) | 71 (91) | 73 (88) |

FIG. 21

METHODS FOR IMPROVING LIPID PROFILES USING ATRASENTAN

CROSS-REFERENCE TO RELATED APPLICATIONS

This application claims the benefit of priority to U.S. Provisional Patent Application Ser. No. 61/817,645, filed Apr. 30, 2013, and to U.S. Provisional Patent Application Ser. No. 61/824,199, filed May 16, 2013. The entire contents of these applications are incorporated herein by reference.

FIELD OF THE DISCLOSURE

The present disclosure is directed to methods for reducing cardiovascular risk in a human subject by administering atrasentan, or a pharmaceutically acceptable salt thereof, in an amount sufficient to effect a reduction of about 5% or more in one or both of (a) total serum cholesterol, relative to the subject's baseline total serum cholesterol, and (b) serum LDL cholesterol, relative to the subject's baseline serum LDL cholesterol.

BACKGROUND OF THE DISCLOSURE

Atrasentan is a potent and selective antagonist for the endothelin A ($ET_A$) receptor. It has been evaluated in clinical trials for the treatment of prostate cancer and also for the treatment of chronic kidney disease (CKD) associated with Type II diabetes. Data reported from such clinical trials has included, for example, fasting glucose, glycosylated hemoglobin level, triglyceride, lipoprotein-A, and uric acid levels in patients receiving atrasentan as compared with those receiving a placebo. (See, e.g., Raichlin, et al., Efficacy and safety of atrasentan in patients with cardiovascular risk and early atherosclerosis. Hypertension; 52: 522-528 (2008)).

Notably, to-date there has been no reporting of clinically significant or therapeutically beneficial effects of atrasentan on low-density lipoprotein (LDL) cholesterol levels in patients receiving it. Inasmuch as the relationship between cholesterol levels, and in particular LDL cholesterol levels, and cardiovascular risk in general, and coronary artery disease in particular, is well recognized, a need continues to exist for additional therapies for reducing cholesterol levels, such as the methods of treatment using atrasentan, as discussed below.

SUMMARY OF THE DISCLOSURE

The present disclosure relates to a method of reducing cardiovascular risk in a human subject, the method comprising administering atrasentan, or a pharmaceutically acceptable salt thereof, in an amount sufficient to effect a reduction of about 5% or more in one or both of (a) total serum cholesterol, relative to a baseline total serum cholesterol of the subject, and (b) serum LDL cholesterol, relative to a baseline serum LDL cholesterol of the subject.

In one embodiment, the present disclosure relates to such a method wherein such a reduction is effected in both (a) total serum cholesterol, relative to a baseline total serum cholesterol of the subject, and (b) serum LDL cholesterol, relative to a baseline serum LDL cholesterol of the subject.

In another embodiment, the present disclosure relates to one or both of the foregoing methods, wherein total serum cholesterol, serum LDL cholesterol, or both, are reduced by about 10% or more, relative to baseline.

In another embodiment, the present disclosure relates to one or both of the foregoing methods, wherein total serum cholesterol, serum LDL cholesterol, or both, are reduced by about 15% or more, relative to baseline.

In another embodiment, the present disclosure relates to one or more of the foregoing methods, wherein the subject is administered a daily dose of about 0.25 mg to about 250 mg, and in one or more particular embodiments is administered a daily dose of about 0.5 mg, about 0.75 mg, about 1.0 mg, or about 1.25 mg.

In another embodiment, the present disclosure related to one or more of the foregoing methods, wherein the subject is suffering from an illness selected from the group consisting of coronary heart disease, hypercholesterolemia, hyperlipidemia, nephropathy, chronic kidney disease, type-2 diabetes, and albuminuria.

In another embodiment, the present disclosure is related to one or more of the foregoing methods, wherein the method further comprises administering a second active agent to the subject, and in one particular embodiment comprises administering a HMG-CoA reductase inhibitor, and in particular a statin, to the subject.

In another embodiment, the present disclosure is related to one or more of the foregoing methods, wherein the method comprises administering a pharmaceutically acceptable salt of atrasentan, and in particular comprises administering atrasentan HCl.

BRIEF DESCRIPTION OF THE DRAWINGS

FIG. 21 is a table illustrating a summary of the demographic information for the combined subject population including the demographic information for each of the three treatment groups (i.e., the placebo (N=50), atrasentan 0.75 mg (N=78), and atrasentan 1.25 mg (N=83) treatment groups), as discussed in Example 7.

Figure 1:
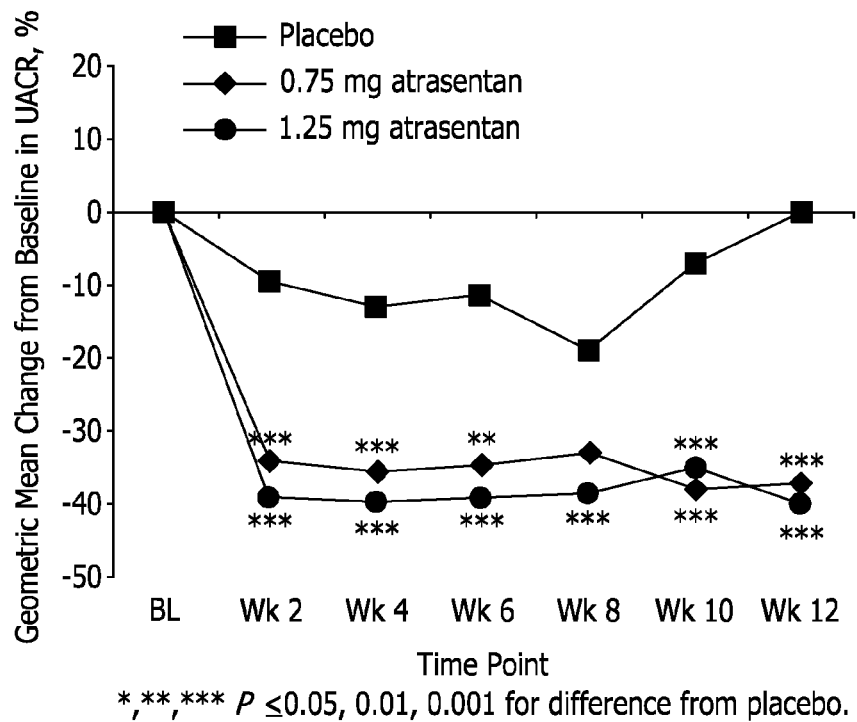
FIG. 1 is a graph illustrating Geometric Mean Change from Baseline in UACR over a 12 week period, as further discussed in Example 1.

It is to be noted that throughout the Figures, *,  and * denote P≤0.05, 0.01 and 0.001, respectively, for difference from placebo (by, for example, MMRM).

DETAILED DESCRIPTION

As further detailed herein below, in according with the present disclosure, atrasentan, or a pharmaceutically acceptable salt thereof, may be advantageously used in a method for reducing cardiovascular risk in a human subject. The method comprises administering atrasentan, or a pharmaceutically acceptable salt thereof, to the subject in an amount sufficient to effect a clinically significant reduction in one or both of (a) total serum cholesterol, relative to a baseline total serum cholesterol of the subject, and (b) serum LDL cholesterol, relative to a baseline serum LDL cholesterol of the subject.

I. Definitions

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number therebetween with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such dosages are thus encompassed by the scope of the claims reciting the terms "about" and "approximately."

The terms "administer", "administering", "administered" or "administration" refer to any manner of providing a drug (such as atrasentan or a pharmaceutically acceptable salt thereof) to a subject. Routes of administration can be accomplished through any form known by those skilled in the art. Such forms include, but are not limited to, oral, buccal, intravenous, subcutaneous, intramuscular, transdermal, by inhalation and the like.

The term "active agent" as used herein refers to an agent (e.g., atrasentan or a pharmaceutically acceptable salt thereof) that achieves a desired biological effect or a pharmaceutically acceptable salt thereof. The term "active agent" and "drug" are used interchangeably herein. The solid state form of the active agent used in preparing the dosage forms of the present disclosure is not believed to be critical. For example, active agent used in preparing the dosage forms of the present disclosure can be amorphous or crystalline. The final dosage form may contain at least a detectable amount of crystalline active agent. The crystalline nature of the active agent can be detected using powder X-ray diffraction analysis, by differential scanning calorimetry or any other techniques known in the art.

The term "atrasentan" refers to the compound (2R,3R,4S)-4-(1,3-benzodioxol-5-yl)-1-[2-(dibutylamino)-2-oxoethyl]-2-(4-methoxyphenyl)pyrrolidine-3-carboxylic acid, which has the structure shown below:

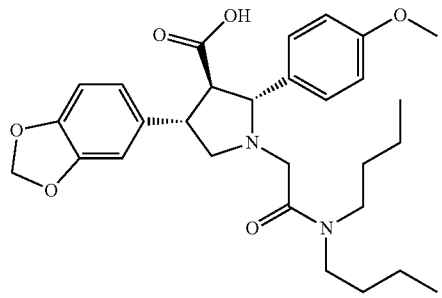 [SMILES: CCCCN(CCCC)C(=O)CN1C[C@H](c2ccc3c(c2)OCO3)[C@@H](C(=O)O)[C@@H]1c1ccc(OC)cc1]

As used herein, the methods of this disclosure are intended to cover administration of this compound, as well as salts thereof (such as the hydrochloride (HCl) salt). Unless otherwise stated, any reference to the amount of atrasentan is based on the weight of the free form of atrasentan. For example, 0.25 mg of atrasentan refers to 0.25 mg of atrasentan in the free form or an equivalent amount of a salt form thereof. Methods for making atrasentan are described, for example, in U.S. Pat. Nos. 6,380,241; 6,946,481; 7,365,093; 5,731,434; 5,622,971; 6,462,194; 5,767,144; 6,162,927; and, 7,208,517. The contents of these patents are incorporated by reference in this application for all relevant and consistent purposes.

The term "baseline," as used herein in the context of total serum cholesterol and/or serum LDL cholesterol levels, refers to the level of total serum cholesterol and/or serum LDL cholesterol of the subject immediately prior to atrasentan administration. In this regard it is to noted that, throughout this disclosure, references to total serum cholesterol and serum LDL cholesterol (baseline or non-baseline results) refer to the concentration thereof in the subject, as determined using means known in the art (and more particularly refers to the concentration of total serum cholesterol or serum LDL cholesterol as determined using standard enzymatic methods and the Friedewald formula, respectively, as known in the art).

The term "dosage form" refers to any solid object, semi-solid, or liquid composition designed to contain a specific pre-determined amount (i.e., dose) of a certain active agent. Suitable dosage forms may be pharmaceutical drug delivery systems, including those for oral administration, buccal administration, rectal administration, topical or mucosal delivery or subcutaneous implants, or other implanted drug delivery systems and the like. In one aspect, the dosage forms of the present disclosure are considered to be solid; however, they may contain liquid or semi-solid components. In another aspect, the dosage form is an orally administered system for delivering an active agent to the gastrointestinal tract of a subject. The dosage form of the present disclosure can exhibit immediate release or modified release of the active agent.

By an "effective amount" or "therapeutically effective amount" of an active agent is meant a sufficient amount of the active agent to provide the desired effect. For example, the daily therapeutically effective or prophylactically effective amount of atrasentan administered to a subject in single or divided dose may be that which is sufficient to achieve or effect a clinically significant reduction in one or both of (a) total serum cholesterol, relative to a baseline total serum cholesterol in the human subject to which it was administered, and (b) serum LDL cholesterol, relative to a baseline serum LDL cholesterol in the human subject to which it was administered. In some embodiments, an "effective amount" or "therapeutically effective amount" may refer to about 0.25 mg to about 250 mg per day, or any amount falling therebetween, which may be administered to the subject in a single or divided dose. In these or other embodiments, this may refer to about 0.5 mg, about 0.75 mg, about 1.0 mg, or about 1.25 mg, per day (or daily) of atrasentan, or an equivalent amount of a pharmaceutically acceptable salt thereof (e.g., atrasentan HCl), in a single or divided dose. Of course, it will be understood by one skilled in the art that other dosage regimens may be utilized, such as dosing more than once per day, utilizing extended, controlled, or modified release dosage forms, and the like in order to achieve the desired result.

By "pharmaceutically acceptable," such as in the recitation of a "pharmaceutically acceptable excipient" or a "pharmaceutically acceptable additive," is meant a material that is not biologically or otherwise undesirable (i.e., the material may be incorporated into a pharmaceutical composition administered to a subject without causing any undesirable biological effects).

The term "RAAS inhibitor" (or "RAS inhibitor") refers to any compound that inhibits one or more elements of the renin-angiotensin-aldosterone system (RAAS). Examples of RAAS inhibitors include ACE inhibitors, ARBs, renin inhibitors, aldosterone antagonists and others.

The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a subject involves prevention of a particular disorder or adverse physiological event in a susceptible individual as well as treatment of a clinically symptomatic individual by inhibiting or causing regression of a disorder or disease.

II. Pharmaceutical Compositions and Dosing Regimens

In one embodiment, the present disclosure relates to novel pharmaceutical compositions and dosing regimens for atrasentan or pharmaceutically acceptable salts thereof. Specifically, the pharmaceutical compositions and dosing regimens of the present disclosure comprise, in one or more embodiments (e.g., embodiments wherein a subject is being treated in order to reduce cardiovascular risk (or another illness or indication associated therewith or related thereto, such as coronary heart disease, hypercholesterolemia, hyperlipidemia, nephropathy, chronic kidney disease, type 2 diabetes, or albuminuria), administering to the subject an amount of atrasentan, or a pharmaceutically acceptable salt thereof, sufficient to effect a reduction of about 5% or more in one or both of (a) total serum cholesterol, relative to baseline total serum cholesterol in the subject, and (b) serum LDL cholesterol, relative to baseline serum LDL cholesterol in the subject. For example, in the present embodiment the subject may be administered about 0.25 mg to about 250 mg of atrasentan, or an equivalent amount of a pharmaceutically acceptable salt thereof, or any individual amount or range falling therebetween, which may be administered to the subject in a single or divided daily dose. In particular embodiments, a dose of about 0.5 mg to about 200 mg, or about 0.5 mg to about 150 mg, or about 0.5 mg to about 100 mg, or about 0.5 mg to about 50 mg, or about 0.5 mg to about 25 mg, or about 0.5 mg to about 15 mg, or about 0.5 mg to about 10 mg, or about 0.5 mg to about 5 mg, or about 0.5 mg to about 2.5 mg, or about 0.5 mg to about 1.5 mg, or about 0.75 mg to about 1.25 mg, of atrasentan, or an equivalent amount of a pharmaceutically acceptable salt thereof, may be administered to the subject per day, in either a single or divide dose. In more particular embodiments, a dose of about 0.5 mg, about 0.75 mg, about 1.0 mg, or even about 1.25 mg, may be administered to the subject per day, in either a single or divided dose.

In this regard it is to be noted that the above-recited doses are exemplary and should not be viewed in a limiting sense, inasmuch as the particular dose or dosing regimen may be optimized for a particular illness or indication, in order to achieve the desired clinically significant reduction in total serum cholesterol, serum LDL cholesterol, or both.

In these or other particular embodiments, the pharmaceutical compositions and dosing regimens of the present disclosure comprises about 0.75 mg of atrasentan or an equivalent amount of a pharmaceutically acceptable salt thereof, such as atrasentan HCl.

In addition to the atrasentan or pharmaceutically acceptable salt thereof, the dosing regimen can also include at least one pharmaceutically acceptable excipient, as further detailed elsewhere herein.

In one or more of the particular embodiments noted herein, a therapeutically effective amount of atrasentan comprises one of the aforementioned dosages per day (i.e., a daily dosage).

The dosing regimen described herein can be used to treat a subject susceptible to or suffering from various illnesses or indications. For example, as previously noted, in one or more embodiments of the present disclosure, atrasentan, or a pharmaceutically acceptable salt thereof, may be administered in order to reduce the cardiovascular risk of a human subject, and more particularly may be administered in order to treat coronary heart disease, hypercholesterolemia, hyperlipidemia, nephropathy, chronic kidney disease, type 2 diabetes, or albuminuria.

In a particular embodiment, the dosing regimen of the present disclosure can be used to treat subjects with nephropathy, and in particular diabetic nephropathy. Advantageously, the dosage may be optimized in order to limiting the undesirable side effects experienced with higher dosing regimens of atrasentan (such as fluid retention, peripheral edema and clinically relevant changes in blood pressure).

The dosing regimen of the present disclosure can be used to treat subjects with diabetic nephropathy while enabling other agents to be used at optimal doses to limit the side effects associated with endothelin receptor antagonists (ETRAs). For example, diuretics may be used in conjunction with atrasentan or a pharmaceutically acceptable salt thereof to control peripheral edema without clinically relevant changes in blood pressure.

The dosing regimen of the present disclosure can be used to treat subjects with albuminuria, and in particular it can be used to treat albuminuria in subjects with diabetic nephropathy, while enabling other agents to be used at optimal doses to treat chronic kidney disease. For example, maximum tolerated doses of one or more RAAS inhibitors may be used in conjunction with atrasentan or a pharmaceutically acceptable salt thereof to treat chronic kidney disease.

In one aspect, the dosing regimen comprises a dosage form comprising a concentration of atrasentan, or an equivalent amount of a pharmaceutically acceptable salt thereof, as recited above. In one particular aspect, the dosing regimen comprises a dosage form comprising about 0.25 mg to about 250 mg atrasentan or a pharmaceutically acceptable salt thereof (or any dosage or dosage range falling therebetween, as previously noted), and more particularly may comprises about 0.5 mg, about 0.75 mg, about 1.0 mg, or about 1.25 mg, of atrasentan or an equivalent amount of a pharmaceutically acceptable salt thereof. In addition to the atrasentan or pharmaceutically acceptable salt thereof, the dosage form can also include at least one pharmaceutically acceptable excipient. Specifically, the atrasentan or a pharmaceutically acceptable salt thereof in said dosage form delivers a dose as recited herein (e.g., about 0.75 mg atrasentan) per day (or daily). The dosage form described herein can be used to treat a subject in need of treatment. For example, in one embodiment, the dosage form can be used to treat subjects with diabetic nephropathy. In another embodiment, the dosage form can be used to reduce cardiovascular risk in subjects.

The dosage forms contemplated for use in the dosing regimen can be immediate release dosage forms, sustained release dosage forms or combinations thereof (such as a sustained release dosage form coated with an immediate release drug coating layer) and contain a therapeutically effective amount and optionally, a pharmaceutically acceptable salt thereof and at least one pharmaceutically acceptable excipient.

As mentioned herein, any dosage form that provides for the immediate release, sustained release or a combined immediate and sustained release of atrasentan or a pharmaceutically acceptable salt thereof can be used in the dosing regimen of the present disclosure. Examples of such dosage forms that can be used include, but are not limited to, matrix systems, membrane controlled systems (which are also referred to as "reservoir systems"), pulse release systems or osmotic pumps. Each of these systems is described in greater detail herein. A detailed discussion of such dosage forms may also be found in: (i) *Handbook of Pharmaceutical Controlled Release Technology*, ed. D. L. Wise, et al., Marcel Dekker, Inc., New York, N.Y. (2000); and (ii) *Treatise on Controlled Drug Delivery, Fundamentals, Optimization, and Applications*, ed. A. Kydonieus, Marcel Dekker, Inc., New York, N.Y. (1992).

Matrix systems are well known to those skilled in the art. For the dosage forms of the present disclosure, atrasentan or a pharmaceutically acceptable salt thereof is homogenously dispersed in at least one rate-controlling mechanism and optionally, with at least one pharmaceutically acceptable excipient. This admixture can be made into a dosage form such as, but not limited to, a powder, a granule, bead, pellet, particulate, a tablet, a mini tablet or an agglomerate. The present disclosure also contemplates that the dosage form, such as, but not limited to, a powder, a granule, bead, pellet, particulate, a tablet, a mini tablet or an agglomerate, can be sprinkled on to food or dissolved in an appropriate drink for subject consumption. The present disclosure also contemplates that after said dosage form is made that it can be optionally surrounded or coated with one or more rate-controlling layers and/or one or more enteric coatings, which will be described in more detail herein.

As used herein, the term "at least one rate-controlling mechanism" refers to an agent that controls or modulates the rate of release of the atrasentan from the dosage form. The at least one rate-controlling mechanism generally includes an inert, non-toxic material that is at least partially, and generally substantially completely erodible in an environment of use. Selection of materials suitable for the rate-controlling mechanism of the present disclosure will depend upon the desired period for the release of the atrasentan from the dosage form which is well known to those skilled in the art.

The rate-controlling mechanism used in a matrix dosage form can be a hydrophilic agent, hydrophobic agents or combinations thereof. Additionally, the rate-controlling mechanism may optionally include any pharmaceutically acceptable excipient that can help modulate the hydrophilicity and/or hydrophobicity of the hydrophilic and/or hydrophobic agents. Hydrophilic agents that can be used include, but are not limited to, celluloses (such as, but not limited to, hydroxypropyl methylcellulose, hydroxypropyl cellulose, hydroxyethyl cellulose), polyethylene oxide, polyethylene glycols ("PEG"), xanthum gum, alginates, polyvinyl pyrrolidone, starches, cross-linked homopolymers and copolymers of acrylic acid and other pharmaceutically acceptable substances with swelling and/or gel-forming properties and combinations thereof. Hydrophobic agents that can be used include, but are not limited to, waxes and water-insoluble agents. Examples of waxes that can be used include, but are not limited to, natural and synthetic waxes, such as, carnauba wax, bees wax, candelilla wax, paraffin waxes and combinations thereof. Water insoluble agents include, but are not limited to, ammoniomethacrylate copolymers (such as Eudragit® RL100 and RS100), cellulose, ethylcellulose, cellulose acetates, cellulose acetate butyrate, cellulose acetate propionate, methacrylic ester copolymers (such as Eudragit® NE30D), microcrystalline cellulose and dibasic calcium phosphate and combinations thereof. Examples of a rate-controlling mechanism used in the form of a coating or membrane include, but are not limited to, ethylcellulose (such as Surelease® and Aquacoat® ECD), ammoniomethacrylate copolymers (such as Eudragit® RL30D and RS30D) and methacrylic ester copolymers (such as Eudragit® NE30D).

One skilled in the art would be able to determine the types and amounts of pharmaceutically acceptable excipients that would be suitable and appropriate for such matrix dosage forms. Examples of pharmaceutically acceptable excipients that can be used in the dosage forms of the present disclosure include, but are not limited to, one or more fillers, binders, lubricants/glidants, solubility enhancing agents, suspending agents, sweetness and/or flavoring agents, preservatives, buffers, wetting agents, disintegrating agents, effervescent agents, surfactants, humectants, solution retarders, absorbents, solvents, other pharmaceutically acceptable additives and combinations thereof.

Fillers that can be used in the present disclosure include, but are not limited to, starches, lactose, microcrystalline cellulose, sucrose, glucose, sorbitol, mannitol and combinations thereof. Examples of fillers that can be used are microcrystalline cellulose, such as Avicel® PH101 and Avicel® PH102; lactose, such as lactose monohydrate, lactose anhydrous and Pharmatosee DCL21; and dibasic calcium phosphate such as Emcompress®.

Binders that can be used in the present disclosure include, but are not limited to, celluloses such as hydroxypropyl methylcellulose, hydroxypropyl cellulose, microcrystalline cellulose, polyvinyl pyrrolidone, starches and other pharmaceutically acceptable substances with cohesive properties.

Lubricants and glidants that can be used in the present disclosure include, but are not limited to, colloidal silicon dioxide, such as Aerosil® 200, talc, stearic acid, magnesium stearate, calcium stearate, solid polyethylene glycols, sodium stearyl fumarate, silica gel and mixtures thereof and other substances with lubricating or gliding properties.

Solubility enhancing agents that can be used include, but are not limited to, co-solvents such as ethanol or propylene glycol, surfactants and polymeric substances such as polysorbates, polyalkylene glycols, poloxamers or polyvinylpyrrolidone, and oily fatty acids and their mono- or diglyceryl esters such as linoleic acid or glyceryl monolaurate.

Suspending agents that can be used include, but are not limited to, carboxymethylcelluose, veegum, tragacanth, bentonite, methylcellulose and polyethylene glycols.

Sweeteners that can be used in the present disclosure are any natural or artificial sweetener such as, but not limited to, sucrose, xylitol, sodium saccharin, cyclamate, aspartame and acesulfame. Examples of flavoring agents are Magnasweet®, bubble gum flavor, fruit flavors and the like.

Preservatives that can be used in the present disclosure include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol or quaternary compounds such as benzalkonium chloride.

Suitable buffers that can be used in the present disclosure include, but are not limited to, phosphate, acetate, citrate, succinate and histidine buffers.

Wetting agents that can be used in the present disclosure include, but are not limited to, ammonium lauryl sulfate and sodium lauryl sulfate.

Suitable disintegrating agents that can be used in the present disclosure include, but are not limited to, cross-linked polyvinyl pyrrolidone, corn starch, potato starch, maize starch and modified starches, agar-agar, calcium carbonate, sodium carbonate, alginic acids, cross-carmellose sodium, sodium starch glycolate, microcrystalline cellulose and mixtures thereof.

Suitable effervescent agents that can be used in the present disclosure are effervescent couples such as, but not limited to, an organic acid and a carbonate or bicarbonate. Suitable organic acids include, but are not limited to, citric, tartaric, malic, fumaric, adipic, succinic, and alginic acids and anhydrides and acid salts. Suitable carbonates and bicarbonates include, but are not limited to, sodium carbonate, sodium bicarbonate, potassium carbonate, potassium bicarbonate, magnesium carbonate, sodium glycine carbonate, L-lysine carbonate and arginine carbonate.

The term "surfactant" is used in its conventional sense in the present disclosure. Any surfactant is suitable, whether it is amphoteric, non-ionic, cationic or anionic. Examples of suitable surfactants include, but are not limited to, sodium lauryl sulfate, polysorbates such as polyoxyethylene sorbitan monooleate, monolaurate, monopalmitate, monostearate or another ester of polyoxyethylene sorbitan (e.g., the commercially available Tweens®, such as, Tween® 20 and Tween® 80 (ICI Speciality Chemicals)), sodium dioctylsulfosuccinate (DOSS), lecithin, stearylic alcohol, cetostearylic alcohol, cholesterol, polyoxyethylene ricin oil, polyoxyethylene fatty acid glycerides, poloxamers (e.g., Pluronics F68® and F108®, which are block copolymers of ethylene oxide and propylene oxide); polyoxyethylene castor oil derivatives or mixtures thereof.

Examples of humectants that can be used, include, but are not limited to, glycerol, sorbitol, pentatol, polyethylene glycol or propylene glycol.

Examples of absorbents that can be used include, but are not limited to, kaolin and bentonite.

The dosage form can optionally be surrounded or coated with at least one non-rate-controlling layer. The functions of the non-rate-controlling layer include, but are not limited to, providing stability for the active agent, functioning as a process aid and/or as a cosmetic enhancement for the formulation. The non-rate-controlling layer can be formed as a single layer, coating or membrane or a plurality of single layers, coatings or membranes.

When the dosage form contains a non-rate-controlling layer, said non-rate-controlling layer can be made of one or more polymers, as well as, other ingredients known in the art, such as, but not limited to, plasticizers, pigments/opacifiers, waxes, etc. Examples of polymers that can be used include, but are not limited to, hydroxypropyl methylcellulose, hydroxypropyl cellulose, methylcellulose, polyvinyl alcohol and polyethylene glycol. Examples of plasticizers that can be used include, but are not limited to, polyethylene glycol(s), glycerin, triacetin, triethyl citrate, diethyl phthalate, and mineral oils. Examples of pigments/opacifiers that can be used include, but are not limited to, water soluble dyes (for example, sunset yellow, quinoline yellow, erythrosine, and tartrazine), pigments (for example, aluminum lakes, titanium oxides, iron oxides and talc), and natural products (for example, riboflavin, carotenoids, chlorophyll, anthocyanins, and carmine). Examples of a wax that can be used include, but are not limited to, a paraffin wax.

Matrix dosage forms can be prepared using standard techniques well known to those skilled in the art, such as direct blending, dry granulation (roller compaction), wet granulation (high shear granulation), milling or sieving, drying (if wet granulation is used), extrusion/spheronization, balling or compression, and, optionally, coating. For example, such dosage forms can be prepared by mixing atrasentan or a pharmaceutically acceptable salt thereof, at least one rate-controlling mechanism, and optionally, at least one pharmaceutically acceptable excipient to obtain a powder blend. The powder blend can then be filled into a capsule or compressed into tablets. Additionally, the powder blend can be further subjected to granulation or extrusion and the granulate or extrudate can be formed into a tablet or filled into a capsule, using routine techniques known in the art.

The present disclosure also contemplates that the matrix dosage forms described herein, can, such as after being filled into capsules or compressed into tablets, be subsequently coated with one or more enteric coatings. The enteric coatings that can be used for such coatings are described in more detail herein. For example, such dosage forms can be prepared by mixing atrasentan or a pharmaceutically acceptable salt thereof and at least one pharmaceutically acceptable excipient to obtain a powder blend. The powder blend can then be enteric coated, can be compressed into a tablet that can be enteric coated or can be filled into a capsule which can be enteric coated. Also, the powder blend can be subjected to further granulation using routine techniques known in the art and the resulting granules coated with an enteric coating. The resulting granules can then be filled into a capsule and the capsule coated with at least one enteric coating, using routine techniques known in the art.

Another system that can be used to make the dosage forms of the present disclosure is a reservoir system. In this system, at least one core containing or comprising atrasentan or a pharmaceutically acceptable salt thereof is coated or layered with at least one pharmaceutically acceptable coating, layer or membrane. The coating, layer or membrane, and its thickness offer a predetermined resistance to atrasentan diffusion from the reservoir to the gastrointestinal tract. Thus, the active agent is gradually released from the core into the GASTROINTESTINAL tract, thereby providing a desired sustained release of the at least one active agent.

As mentioned briefly above, reservoir systems and methods for making such dosage forms are well known in the art. For example, U.S. Pat. Nos. 5,286,497 and 5,737,320, both of which are hereby incorporated by reference, describe such dosage forms and their methods of production. In the dosage forms of the present disclosure, the core(s) can be a granule, bead, pellet, particulate, microsphere, mini tablet, tablet or agglomerate. The core can be made in a variety of different ways. For example, the core can comprise a mixture of atrasentan or a pharmaceutically acceptable salt thereof and at least one of the rate-controlling mechanisms described previously herein and, optionally, at least one of the pharmaceutically acceptable excipients described previously herein. Alternatively, the core can comprise atrasentan or a pharmaceutically acceptable salt thereof and, optionally, at least one pharmaceutically acceptable excipient and can be further surrounded or coated with at least one rate-controlling mechanism. Alternatively, the core can comprise an inert substrate onto which is applied atrasentan or a pharmaceutically acceptable salt thereof and, optionally, at least one pharmaceutically acceptable excipient. In addition, the substrate can be further surrounded or coated with at least one rate-controlling mechanism, at least one non-rate-controlling layer, at least one enteric coating or any combinations thereof.

Optionally, the core may also contain one or more non-rate-controlling layers as described previously herein. The location of the non-rate-controlling layer in the formulation is not critical. For example, the non-rate-controlling layer may be present between the core and an enteric coating or other polymeric coating. Alternatively, the non-rate-controlling layer may surround or coat an enteric coating or other polymeric coating.

The core can be produced by using routine techniques known in the art such as, but not limited to, direct blending, dry granulation (roller compaction), wet granulation (high shear granulation), milling or sieving, drying (if wet granulation is used), extrusion/spheronization, balling or compression, and, optionally, coating.

The second major component of a reservoir system is at least one coating, layer or membrane for use in controlling the release of the atrasentan from the dosage form. An example of a coating, layer or membrane that can be used is a polymeric coating. Examples of suitable polymers that can be used include, but are not limited to, ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly (propylene), poly(ethylene oxide), poly(ethylene terephthalate), poly(vinyl isobutyl ether), poly(vinyl acetate), poly(vinyl chloride) or polyurethane or mixtures thereof.

The polymeric coating may be applied to the core using methods and techniques known in the art. Examples of suitable coating devices include fluid bed coaters and pan coaters. Application techniques are described in more detail in: i) *Aqueous polymeric coatings for pharmaceutical compositions*, ed. J. W. McGinity, Marcel Dekker, Inc., New York, N.Y. (1997); and ii) *Pharmaceutical compositions: Tablets* Vol. 3. ed. H. A. Lieberman, L. Lachman and J. B. Schwartz, Marcel Dekker, Inc., New York, N.Y. pp. 77-287, (1990).

Another coating, layer or membrane that can be applied to the core is at least one enteric coating. One or more enteric coatings can be applied on to the core (the core may or may not contain one or more rate-controlling layers, non-rate-controlling layers or combinations of rate-controlling layers and non-rate controlling layers). For example, an enteric coating may be dispersed or dissolved in either water or in a suitable organic solvent and then sprayed on to the core or applied as a dry coating on to the core. Any enteric coating can be used in the present disclosure, including, but not limited to, solutions or dispersions of methacrylic acid and methacrylic ester copolymers, cellulose acetate phthalate, hydroxypropyl methylcellulose phthalate, hydroxypropyl methylcellulose acetate succinate, polyvinyl acetate phthalate, ethyl acrylate/methacrylic acid copolymers, cellulose acetate trimellitate, shellac and combinations thereof. For environmental reasons, aqueous based coatings can be used in the present disclosure as well. Examples of aqueous based coatings that can be used include, but are not limited to, methacrylic acid and methacrylic ester copolymers, hydroxypropyl methylcellulose acetate succinate, ethyl acrylate/methacrylic acid copolymers, cellulose acetate phthalate and combinations thereof.

The enteric coating can be formed as a single or multiple layers. The thickness of the coating can be readily determined by those skilled in the art, but must be sufficient to protect the dosage form in the acidic environment of the stomach.

The enteric coating(s) may contain one or more pharmaceutically acceptable plasticizers (in order to obtain desirable mechanical properties, such as, but not limited to, improved flexibility and strength of the enteric coating), such as, but not limited to, triacetin, citric acid esters, phthalic acid esters, dibutyl sebacate, cetyl alcohol, polyethylene glycols and polysorbates. The type and amount of plasticizer used will depend upon the intended composition of the enteric coating and can be readily determined by one skilled in the art. In addition to one or more plasticizers, the enteric coating can also contain anti-caking agents such as talc, as well as disperants, colorants, pigments, anti-foaming agents as well as other pharmaceutically acceptable agents to increase the thickness of the enteric coating and/or to regulate or modulate the diffusion of acidic gastric juices into the core.

If one or more enteric coatings are used, a coating between the core and the enteric coating can also be used (such a coating is frequently referred to as a "subcoating"). Any film forming polymer can be used as a subcoating. For example, polymers such as polyvinyl alcohol, hydroxypropyl cellulose and/or hydroxypropyl methyl cellulose can be used.

In an osmotic pump system, a core is encased by a semipermeable membrane having at least one orifice. The semipermeable membrane is permeable to water, but impermeable to the active agent. When the system is exposed to body fluids, water will penetrate through the semipermeable membrane into the tablet core containing osmotic excipients and at least one active agent. Osmotic pressure increases within the dosage form and the atrasentan is released through the orifice in an attempt to equalize pressure.

In more complex pumps, the core can contain multiple internal compartments. For example, the first compartment may contain at least one active agent and the second compartment may contain at least one polymer that swells on contact with fluid. After ingestion, the polymer swells into the active agent containing compartment at a predetermined rate and forces the atrasentan from the dosage form at that rate.

Pulsed release systems are also well known to those skilled in the art. Pulsed release systems release at least one active agent in pulses (namely, at different time points). Pulsed release systems also may include a combination of immediate release and extended release. Multiple configurations are suitable for pulsed release dosage forms of the atrasentan.

Osmotic pumps are well known in the art and have been described in the literature. For example, U.S. Pat. Nos. 4,088,864, 4,200,098, and 5,573,776; all of which are hereby incorporated by reference, describe osmotic pumps and methods for their manufacture.

Generally, osmotic pumps are typically formed by compressing a tablet of an osmotically active drug (or an osmotically inactive drug in combination with an osmotically active agent or osmagent) and then coating the tablet with a semipermeable membrane that is permeable to an exterior aqueous-based fluid but impermeable to the passage of drug and/or osmagent. One or more delivery orifices may be drilled through the semipermeable membrane wall. Alternatively, orifice(s) through the wall may be formed in situ by incorporating leachable pore forming materials in the wall. In operation, the exterior aqueous based fluid is imbibed through the semipermeable membrane wall and contacts with at least one active agent to form a solution or suspension of the active agent. The active agent solution or suspension is then "pumped" out through the orifice as fresh fluid is imbibed through the semipermeable membrane.

As mentioned previously herein, osmotic pumps may contain multiple distinct compartments. The first compartment may contain the atrasentan as described above, and the second compartment may contain an expandable driving member consisting of a layer of a swellable hydrophilic polymer, which operates to diminish the volume occupied by the active agent, thereby delivering the atrasentan from the device at a controlled rate over an extended period of time. Alternatively, the compartments may contain separate doses of at least one active agent.

Semipermeable membranes that can be used include, but are not limited to, semipermeable polymers known in the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876, 3,276,586, 3,541,005, 3,541,006, and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 50%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020.

The osmotic agent present in the pump, which may be used when at least one active agent itself is not sufficiently osmotically active, are osmotically effective compounds soluble in the fluid that enters the pump, and exhibit an osmotic pressure gradient across the semipermeable wall against the exterior fluid. Osmotically effective osmagents useful for the present purpose include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, mixtures thereof, and the like. The osmagent can be present in an excess amount, and it can be in any physical form, such as particle, powder, granule, and the like. The osmotic pressure in atmospheres of osmagents suitable for the invention will be greater than zero and generally up to about 500 atm or higher.

The expandable driving member can be a swellable, hydrophilic polymer which interacts with water and aqueous biological fluids and swells or expands to an equilibrium state. The polymers exhibit the ability to swell in water and retain a significant portion of the imbibed water within the polymer structure. The polymers swell or expand to a very high degree, usually exhibiting a 2 to 50 fold volume increase. The polymers can be cross-linked or may not be cross-linked. The swellable, hydrophilic polymers can be lightly cross-linked, such cross-links being formed by covalent ionic bonds or hydrogen bonds. The polymers can be of plant, animal or synthetic origin. Hydrophilic polymers that can be used in the present disclosure include, but are not limited to, poly(hydroxy alkyl methacrylate) having a molecular weight from 30,000 to 5,000,000; kappa carrageenan, polyvinylpyrrolidone having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose; cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.001 to about 0.5 moles of saturated cross-linking agent per mole of maleic anhydride in copolymer; water swellable polymers of N-vinyl lactams, and the like.

The term "orifice" as used herein refers to means and methods suitable for releasing the atrasentan from an osmotic system. The expression includes one or more apertures or orifices which have been bored through the semipermeable membrane by mechanical procedures. Alternatively, the orifice can be formed by incorporating an erodible element, such as a gelatin plug, in the semipermeable membrane. In cases where the semipermeable membrane is sufficiently permeable to the passage of active agent, the pores in the membrane may be sufficient to release atrasentan in amounts sufficient to meet the plasma threshold. In such cases, the term "passageway" refers to the pores within the membrane wall even though no bore or other orifice has been drilled through. A detailed description of osmotic passageways and the maximum and minimum dimensions for a passageway are disclosed in U.S. Pat. Nos. 3,845,770 and 3,916,899, the disclosures of which are incorporated herein by reference.

Osmotic pumps can be made using routine techniques known to those skilled in the art. For example, the atrasentan or pharmaceutically acceptable salt thereof, at least one rate-controlling mechanism and optionally at least one pharmaceutically acceptable excipient may be housed in one area of the compartment adjacent to the passageway, are pressed into a solid having a dimension that corresponds to the internal dimensions of the area of the compartment the atrasentan will occupy, or the atrasentan, rate-controlling mechanism and excipients and a solvent are mixed into a solid or semisolid form by conventional methods such as, but not limited to, ball milling, calendaring, stirring or roll milling, and then pressed into a preselected shape. Next, a layer of a hydrophilic polymer is placed in contact with the layer of drug in a like manner, and the two layers surrounded with a semipermeable wall. The layering of drug formulation and hydrophilic polymer can be fabricated by conventional two-layer press techniques. The wall can be applied by molding, spraying or dipping the pressed shapes into a wall forming material. Another technique that can be used for applying the wall is the air suspension procedure. This procedure consists of suspending and tumbling the pressed agent and dry hydrophilic polymer in a current of air and a wall forming composition until the wall is applied to the agent-hydrophilic polymer composite. The air suspension procedure is described in U.S. Pat. No. 2,799,241; J. Am. Pharm. Assoc., 48:451-459 (1979). Other manufacturing procedures are described in Modern Plastics Encyclopedia, Vol. 46, pp. 62-70 (1969); and in Pharmaceutical Sciences, by Remington, Fourteenth Edition, pp. 1626-1678 (1970), published by Mack Publishing Company, Easton, Pa.

III. Methods of Treatment

As previously noted, the present disclosure is directed in one embodiment to a method of reducing cardiovascular risk in a human subject, the method comprising administering atrasentan, or a pharmaceutically acceptable salt thereof, in an amount sufficient to effect a reduction of about 5% or more in one or both of the subject's total serum cholesterol and serum LDL cholesterol, relative to the subject's baseline level(s) thereof, and in some instances may be sufficient to effect a reduction of about 10%, about 15%, about 20%, about 25%, or more, relative to baseline, in one or both of the subject's total serum cholesterol and serum LDL cholesterol.

In this regard it is to be noted that a reduction in one or both of total serum cholesterol and serum LDL cholesterol may be any percentage falling within a range bound by any two of the percentages recited above without departed from the scope of the present disclosure (e.g. a reduction of about 5% to about 25%, or about 5% to about 10%, or about 10% to about 20%, or about 10% to about 25%, etc., relative to baseline). In one or more particular embodiments, however, the reduction in one or both of total serum cholesterol and serum LDL cholesterol may be about 5% to about 25%, or about 10% to about 25%, or about 15% to about 25%, relative to baseline.

In this regard is it to be further noted that when a reduction in both total serum cholesterol and serum LDL cholesterol occurs, the reduction in each may be the same or different; accordingly, the present method may effect a reduction in total serum cholesterol and/or serum LDL cholesterol in any combination or permutation possible here, without departing from the intended scope of the present disclosure (e.g., a total serum cholesterol reduction of about 15% and serum LDL cholesterol reduction of about 10%; a total serum cholesterol reduction of about 20% and serum LDL cholesterol reduction of about 10%; a total serum cholesterol reduction of about 10% and serum LDL cholesterol reduction of about 15%; a total serum cholesterol reduction of about 15% and serum LDL cholesterol reduction of about 20%; a total serum cholesterol reduction of about 10% and serum LDL cholesterol reduction of about 10%; a total serum cholesterol reduction of about 15% and serum LDL cholesterol reduction of about 15%; etc.).

It is to be further note that the method of the present disclosure may be used to treat, for example, a subject susceptible to or suffering from coronary heart disease, hypercholesterolemia, hyperlipidemia, nephropathy, chronic kidney disease, diabetes (e.g., type 2 diabetes) or albuminuria, by administering thereto a dose of atrasentan, or a pharmaceutically acceptable salt thereof, sufficient to effect such a reduction in the subject's total serum cholesterol, serum LDL cholesterol, or both, relative to the subject's baseline level(s) thereof. More generally, the method of the present disclosure may be used to treat a subject susceptible to or suffering from any illness or complication related to elevated levels of total serum cholesterol and/or serum LDL cholesterol. As such, the method of the present disclosure may be administered to a human subject in a dose sufficient to effect a reduction in one or both of total serum cholesterol and LDL cholesterol, relative to baseline, of about 10 mg/dL, about 15 mg/dL, about 20 mg/dL, about 25 mg/dL, or more.

In this regard it is to be noted that a reduction in one or both of total serum cholesterol and serum LDL cholesterol may be any amount falling within a range bound by any two of the amounts recited above without departed from the scope of the present disclosure (e.g. a reduction of about 10 mg/dL to about 25 mg/dL, or about 10 mg/dL to about 20 mg/dL, or about 15 mg/dL to about 20 mg/dL, or about 20 mg/dL to about 25 mg/dL, etc.). In one or more particular embodiments, however, the reduction in one or both of total serum cholesterol and serum LDL cholesterol may be about 10 mg/dL to about 25 mg/dL, or about 15 mg/dL to about 25 mg/dL, or about 20 mg/dL to about 25 mg/dL, relative to baseline.

In this regard is it to be further noted that when a reduction in both total serum cholesterol and serum LDL cholesterol occurs, the reduction in each may be the same or different; accordingly, the present method may effect a reduction in total serum cholesterol and/or serum LDL cholesterol in any combination or permutation possible here, without departing from the intended scope of the present disclosure (e.g., a total serum cholesterol reduction of about 15 mg/dL and serum LDL cholesterol reduction of about 10 mg/dL; a total serum cholesterol reduction of about 20 mg/dL and serum LDL cholesterol reduction of about 10 mg/dL; a total serum cholesterol reduction of about 10 mg/dL and serum LDL cholesterol reduction of about 15 mg/dL; a total serum cholesterol reduction of about 15 mg/dL and serum LDL cholesterol reduction of about 20 mg/dL; a total serum cholesterol reduction of about 15 mg/dL and serum LDL cholesterol reduction of about 15 mg/dL; a total serum cholesterol reduction of about 25 mg/dL and serum LDL cholesterol reduction of about 25 mg/dL; etc.).

The dosing regimen may be as described elsewhere herein (e.g., from about 0.25 mg to about 250 mg, or any amount falling therebetween, of atrasentan or a pharmaceutically acceptable salt thereof, as detailed elsewhere herein).

In another aspect, the present disclosure may alternatively relate to methods of treating a renal clinical endpoint in a subject suffering from diabetic nephropathy or nondiabetic kidney disease by administering to a subject in need thereof, a dosing regimen as described previously (which contains a therapeutically effective amount of atrasentan or a pharmaceutically acceptable salt thereof). The therapeutically effective amount of atrasentan is about 0.75 mg per day (or daily) or an equivalent amount in a pharmaceutically acceptable salt form.

In yet another aspect, the present disclosure relates to methods of treating a renal clinical endpoint in subjects with diabetic nephropathy or nondiabetic kidney disease by administering to a subject in need of treatment thereof, a dosing regimen that comprises a dosage form comprising a therapeutically effective amount of atrasentan or a pharmaceutically acceptable salt thereof as also described previously. Specifically, in addition to the atrasentan or pharmaceutically acceptable salt thereof, the dosage form employed in the dosing regimen can also include at least one pharmaceutically acceptable excipient. Specifically, the therapeutically effective amount of atrasentan or a pharmaceutically acceptable salt thereof in said dosage form delivers a dose of atrasentan of about 0.75 mg per day (or daily).

Diabetic nephropathy may be identified by various measures such as subjects with type 2 diabetes and nephropathy defined as an estimated glomerular filtration rate (eGFR) of 25 to 75 ml/min/1.73 m2 with UACR>300 mg/g.

The atrasentan or the dosage forms comprising atrasentan may be administered to a subject by any suitable method, manner or route. For example atrasentan HCl may be administered in a dosage form orally, buccally, intravenously, subcutaneously, intramuscularly, transdermally, by inhalation and the like. In one aspect, the dosage form is administered to a subject (such as a subject suffering diabetic neuropathy), orally, once a day, as a single dosage form. The timing of the administration of the dosage form is not believed to be critical. In addition, the methods of the present disclosure are not limited to the administration of the dosage forms comprising about 0.5 mg, about 0.75 mg, about 1.0 mg or about 1.25 atrasentan (or pharmaceutically acceptable salt thereof).

The methods of the present disclosure also contemplate the treatment of a subject with the dosage forms of the present disclosure in combination with one or more additional therapeutic agents. The one or more additional therapeutic agents may be administered simultaneously with the dosage form of the present disclosure or sequentially with the dosage form of the present disclosure. The additional therapeutic agent can be for diabetes, a therapeutic agent can be for diabetic complications, a therapeutic agent can be for hyperlipidemia, a therapeutic agent can be for hypercholesterolemia, an antihypertensive agent, an antiobesity agent, a diuretic, a chemotherapeutic agent, an immunotherapeutic agent, an antithrombotic agent, a therapeutic agent for osteoporosis, a antidementia agent, a therapeutic agent for pollakiuria or urinary incontinence, a therapeutic agent for dysuria and the like. Examples of such additional therapeutic agents were described above.

IV. Co-Administration

As mentioned previously herein, the present disclosure encompasses any dosage forms suitable for oral administration including, but are not limited to, capsules, tablets, pills, powders, etc. Liquid dosage forms for oral administration are also contemplated herein and include, but are not limited to, pharmaceutically acceptable emulsions, solutions, suspensions or syrups.

Additionally, the dosage forms of the present disclosure can be administered alone, or in combination with one or more additional therapeutic, prophylactic or diagnostic agents. The one or more additional therapeutic agents may be used together with the dosage form of the present disclosure or sequentially with the dosage form of the present disclosure. For example, the additional therapeutic agent can be for diabetes, a therapeutic agent can be for diabetic complications, a therapeutic agent can be for hypercholesterolemia, a therapeutic agent can be for hyperlipidemia, an antihypertensive agent, an antiobesity agent, a diuretic, a chemotherapeutic agent, an immunotherapeutic agent, an antithrombotic agent, a therapeutic agent for osteoporosis, an antidementia agent, a therapeutic agent for pollakiuria or urinary incontinence, a therapeutic agent for dysuria and the like.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Vildagliptin, Sitagliptin, Saxagliptin, alogliptin, T-6666, TS-021), β3 agonists (e.g., AJ-9677), GPR40 agonists (e.g., TAK-875), GLP-1 receptor agonists [e.g., GLP-1, GLP-1MR agent, NN-2211, AC-2993 (exendin-4), BIM-51077, Aib(8,35)hGLP-1(7,37)NH2, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-hydroxysteroid dehydrogenase inhibitors (e.g., BVT-3498), adiponectin or agonists thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agents for diabetic complications include aldose reductase inhibitors (e.g., Tolrestat, Epalrestat, Zenarestat, Zopolrestat, Minalrestat, Fidarestat, CT-112, ranirestat (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), stimulators (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agents for hypercholesterolemia and/or hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol), cholesterol absorption inhibitors or blockers (e.g., ezetimibe), and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine, renin inhibitors such as aliskiren, and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonists), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), feeding deterrents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferons, interleukins (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the dosage forms of the present disclosure.

It will be readily apparent to those skilled in the art that other suitable modifications and adaptations of the methods of the present disclosure described herein are enabled and may be made using suitable equivalents without departing from the scope of the present disclosure or the embodiments disclosed herein. Having now described the present disclosure in detail, the same will be more clearly understood by reference to the following examples which are included for purposes of illustration only and not intended to limit the scope of the present disclosure. The disclosures of all journal references, U.S. patents and publications referred to herein are hereby incorporated by reference in their entireties for all relevant and consistent purposes.

There were 153 subjects randomized (1:2:2) into 3 treatment groups: 1) placebo, 2) atrasentan 0.75 mg/day, and 3) atrasentan 1.25 mg/day.

Demographic information for the subjects is set forth in Table 1. There were no statistically significant differences between treatment groups in demographics or baseline characteristics. The requirement that the subjects be taking a maximum tolerated labeled dose of a RAS inhibitor is reflected in the range of blood pressure at study entry of 136-138/71-74 mmHg Approximately 80% of the subjects were taking diuretics at baseline (86.7% in the placebo group, 83.1% in the atrasentan 0.75 mg group, and 73% in the atrasentan 1.25 mg group).

TABLE 1

Demographics and Baseline Characteristics in Example 1

| | Number (%) of Subjects | | |
|---|---|---|---|
| | | Atrasentan | |
| Variable | Placebo N = 30 | 0.75 mg N = 59 | 1.25 mg N = 64 |
| Sex | | | |
| Female | 8 (26.7) | 10 (16.9) | 17 (26.6) |
| Male | 22 (73.3) | 49 (83.1) | 47 (73.4) |
| Race | | | |
| White | 23 (76.7) | 36 (61.0) | 38 (59.4) |
| Black | 2 (6.7) | 14 (23.7) | 13 (20.3) |
| Asian | 4 (13.3) | 6 (10.2) | 9 (14.1) |
| Age, yr | | | |
| Mean (SD) | 63.0 (8.48) | 64.3 (9.60) | 64.0 (9.04) |
| Weight, kg | | | |
| Mean (SD) | 94.8 (18.1) | 92.8 (21.5) | 92.7 (17.3) |
| BMI, kg/m$^2$ | | | |
| Mean (SD) | 32.3 (5.5) | 31.8 (5.5) | 32.4 (5.3) |
| UACR, mg/g creatinine | | | |
| Mean (SD) | 830.85 (565.81) | 1130.54 (817.68) | 1010.31 (733.82) |
| UACR, log/mg/g creatinine | | | |
| Mean (SD) | 6.47 (0.76) | 6.76 (0.76) | 6.68 (0.71) |
| eGFR, mL/min/BSA | | | |
| Mean (SD) | 46.40 (13.43) | 46.03 (14.07) | 48.70 (12.15) |
| Systolic blood pressure, mmHg | | | |
| Mean (SD) | 138.03 (13.79) | 138.51 (13.47) | 136.35 (14.40) |
| Diastolic blood pressure, mmHg | | | |
| Mean (SD) | 71.87 (10.46) | 74.21 (9.40) | 73.98 (9.21) |

Example 1

This example reports a Phase 2b clinical study, in which two doses of atrasentan were evaluated: 0.75 mg and 1.25 mg (both QD). It was a randomized, double-blind, parallel-design, placebo-controlled, 12-week, multicenter study to select an effective atrasentan dose for lowering UACR with minimal effect on fluid retention and lowering blood pressure in subjects with type 2 diabetes and nephropathy who are receiving maximum tolerated labeled doses of a RAS inhibitor and a diuretic, unless medically contraindicated.

Twenty subjects discontinued prematurely from the study. A higher percentage of subjects in the atrasentan groups (13.6% with atrasentan 0.75 mg and 15.6% with atrasentan 1.25 mg) than in the placebo group (6.7%) discontinued from the study. Twelve subjects overall in the atrasentan groups (5 in 0.75 mg group and 7 in 1.25 mg group) discontinued because of an adverse event compared with no subjects in the placebo group.

The primary efficacy endpoint was the change from baseline to Week 12 in log-transformed UACR with the primary analysis conducted using mixed-effects, maximum likelihood, repeated measures (MMRM) with fixed effects for treatment, country, visit, and treatment-by-visit interaction, with baseline measurement and baseline-by-visit interaction as covariates. The results showed that both doses of atrasentan resulted in clinically meaningful and statistically significant reductions in UACR relative to placebo starting at Week 2 and remained stable up to Week 12 (FIG. 1). Both doses of atrasentan reduced UACR by more than 30% within 2 weeks and this reduction was sustained over 12 weeks of treatment.

Secondary efficacy endpoints in Example 1 included the following analyses: the treatment group differences in change from baseline to final measurement in log-transformed UACR; the treatment group differences in change from baseline to each postbaseline measurement for eGFR; the proportion of subjects who achieve a 30%, 40%, or 50% reduction from baseline to final measurement for UACR; the proportion of subjects who achieve at least 30% reduction from baseline to final measurement for UACR and who have not had a treatment-emergent moderate or severe adverse event edema of any kind (including edema, pulmonary edema, etc.); and the proportion of subjects who have changed from macroalbuminuria (UACR≥300 mg/g) at Baseline to microalbuminuria (UACR<300 mg/g) at final value with at least 20% reduction.

The results of a secondary efficacy analysis on log-transformed UACR of change from baseline to final on-treatment measurement are presented in Table 2. The geometric mean reduction was 37.7% for atrasentan 0.75 mg and 40.7% for atrasentan 1.25 mg compared with 0.75% with placebo (P<0.001 for both doses).

surement and who did not have a treatment-emergent moderate or severe adverse event edema was statistically significantly higher in both atrasentan groups compared with placebo (Table 4).

TABLE 4

Percentage of Subjects with 30% Reduction in UACR from Baseline to Final Measurement and with No Moderate or Severe Adverse Event of Edema in Example 1

| Treatment Group | N | Number (%) of Subjects Had ≥30% Reduction in UACR and No Edema | P Value |
|---|---|---|---|
| Placebo | 28 | 4 (14.3) | |
| Atrasentan 0.75 mg | 57 | 27 (47.4) | 0.004 |
| Atrasentan 1.25 mg | 61 | 28 (45.9) | 0.004 |

Note:
P value is for difference from placebo by Fisher's exact test.

Figure 2:
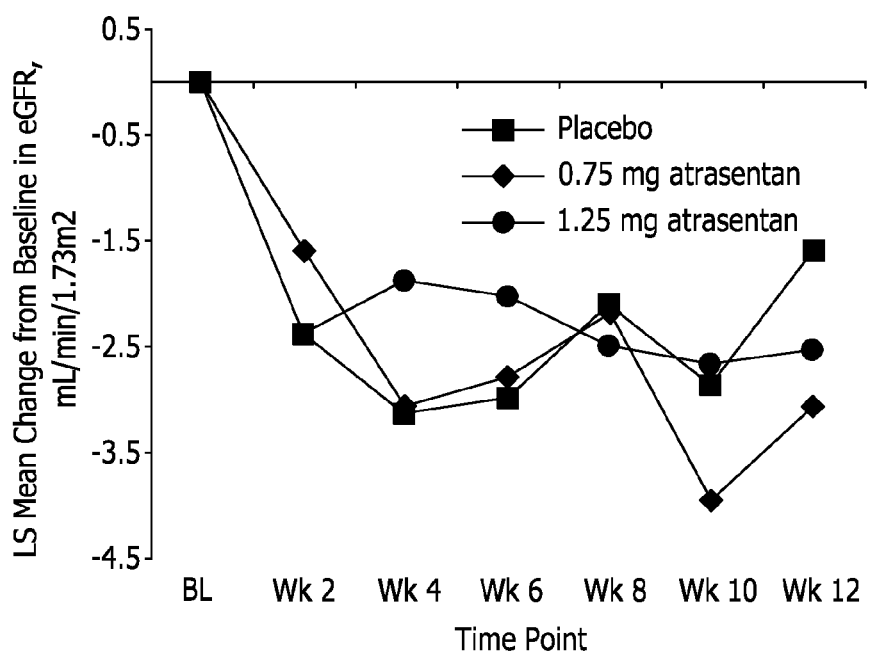
FIG. 2 is a graph illustrating Least Squares (LS) Mean Changes in eGFR from Baseline over time, as further discussed in Example 1.

Mean eGFR decreased from baseline to each postbaseline time point in all treatment groups, with no statistically significant differences between the atrasentan treatment groups and placebo (FIG. 2).

Mean systolic blood pressure decreased from baseline in all treatment groups at Week 1, with some recovery toward

TABLE 2

Mean Change from Baseline to Final On-Treatment Measurement in UACR in Example 1

| | | | Change from Baseline | | Between-group | |
| | | Baseline | LS Mean (SE) | Geometric | Comparison | |
| Treatment Group | N | (log mg/g creatinine) | (log mg/g creatinine) | Mean Change (Percent) | Difference (90% CI) | P Value |
|---|---|---|---|---|---|---|
| Placebo | 28 | 6.47 | −0.01 (0.14) | −0.75% | | |
| Atrasentan 0.75 mg | 58 | 6.76 | −0.47 (0.12) | −37.77% | −0.47 (−0.71, −0.22) | <0.001 |
| Atrasentan 1.25 mg | 64 | 6.68 | −0.52 (0.11) | −40.67% | −0.51 (−0.75, −0.28) | <0.001 |

Note:
P value is from ANCOVA with treatment and country as main effects and baseline measure as the covariate.

The percentage of subjects who experienced at least a 30% reduction from baseline in log-transformed UACR was statistically significantly different from placebo for both doses of atrasentan. A similarly statistically significantly higher percentage of subjects in both atrasentan groups experienced at least a 40% reduction and a 50% reduction in log-transformed UACR compared with placebo (Table 3).

TABLE 3

Percentage of Subjects with Reduction in Log-Transformed UACR from Baseline to Final Measurement in Example 1

| Treatment Group | N | ≥30% Reduction | | ≥40% Reduction | | ≥50% Reduction | |
| | | Yes | P Value | Yes | P Value | Yes | P Value |
|---|---|---|---|---|---|---|---|
| Placebo | 28 | 14.3% | | 7.1% | | 3.6% | |
| Atrasentan 0.75 mg | 57 | 50.9% | 0.002 | 38.6% | 0.002 | 29.8% | 0.005 |
| Atrasentan 1.25 mg | 61 | 52.5% | 0.001 | 36.1% | 0.004 | 29.5% | 0.005 |

Note:
P value is for difference from placebo by Fisher's exact test.

Figure 3:
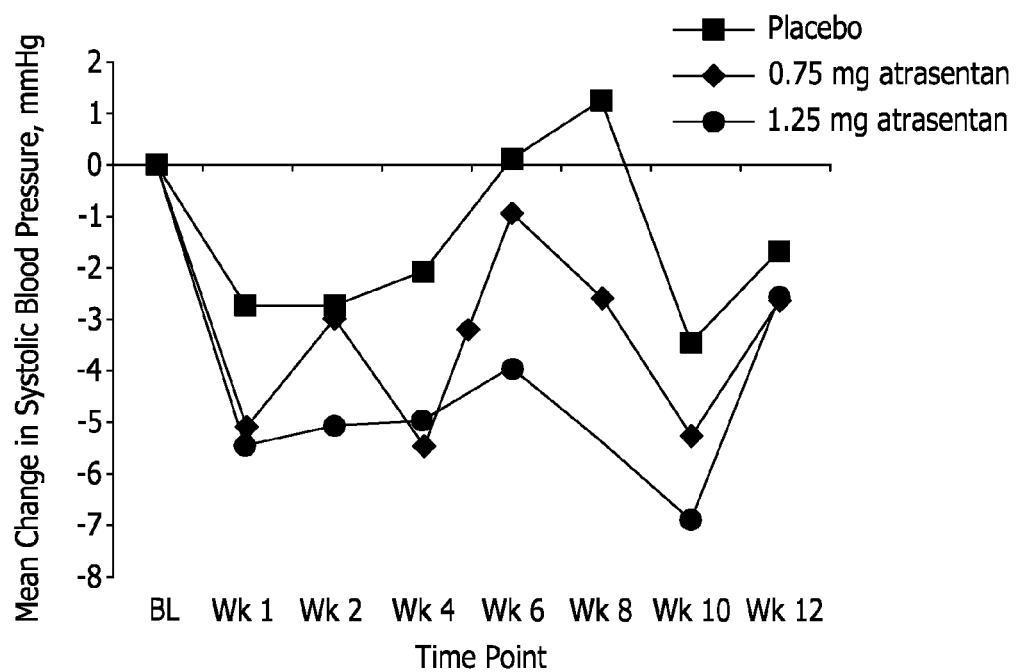
FIG. 3 is a graph illustrating Mean Systolic Blood Pressure Changes from Baseline over time, as further discussed in Example 1.

The percentage of subjects who experienced at least a 30% reduction in UACR from baseline to the final meabaseline values at Weeks 6 and 12. The difference from baseline for atrasentan 0.75 mg was statistically significant at Week 4 and for atrasentan 1.25 mg, the difference was statistically significant at Weeks 1, 8, and 10, but the differences from placebo were not statistically significant at any time point (FIG. 3).

Figure 4:
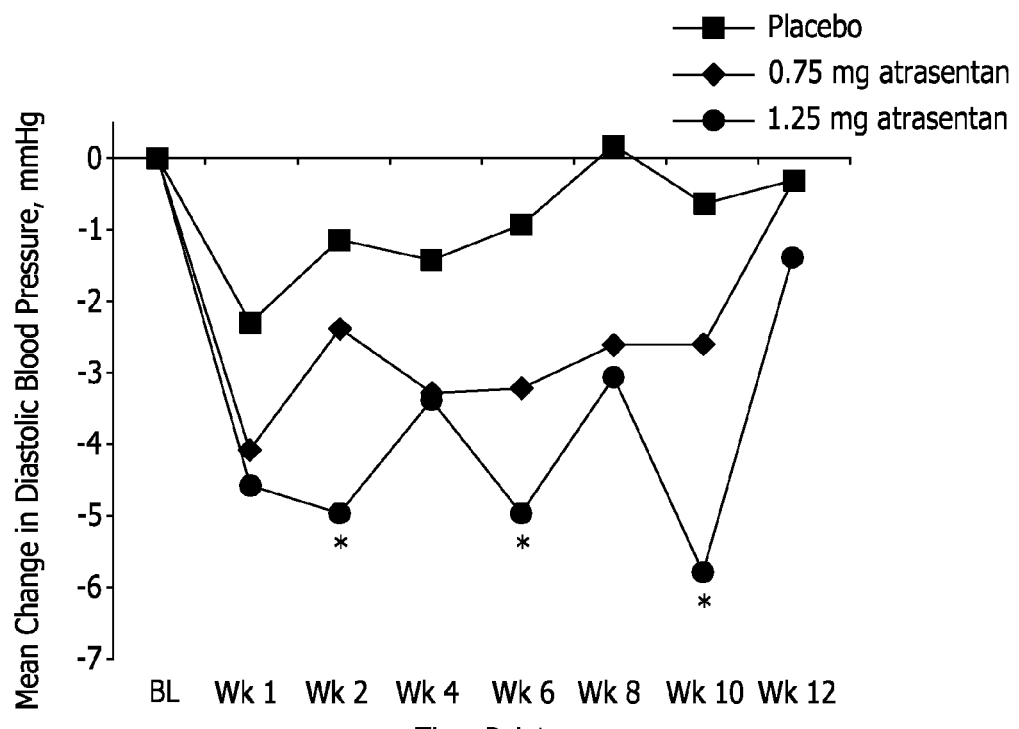
FIG. 4 is a graph illustrating Mean Diastolic Blood Pressure Changes from Baseline over time, as further discussed in Example 1.

Mean diastolic blood pressure decreased from baseline in all treatment groups at Week 1 and then fluctuated over time, with some recovery toward baseline values at Week 12. The difference from baseline for atrasentan 0.75 mg was statistically significant at Weeks 1, 4, and 6 and for atrasentan 1.25 mg, the difference was statistically significant from Weeks 1 through 10. The difference from placebo was statistically significant for the atrasentan 1.25 mg group at Weeks 2, 6, and 10 (FIG. 4).

Figure 5:
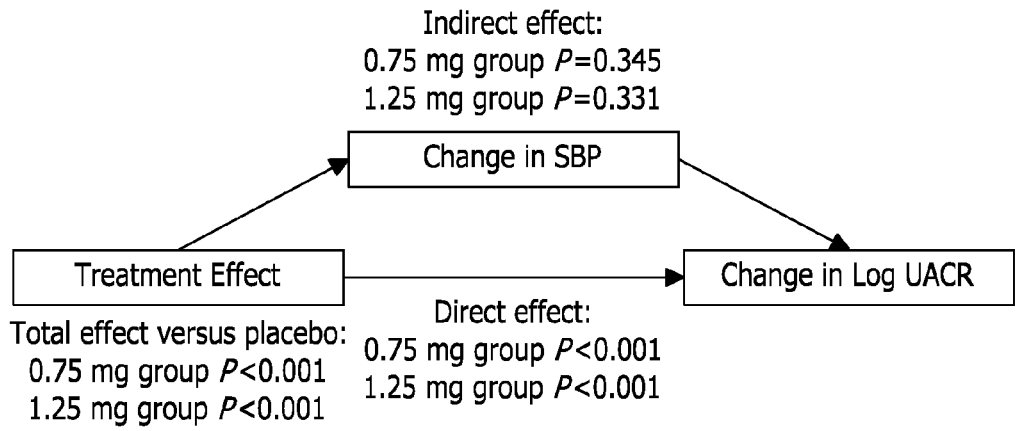
FIG. 5 is a flow chart illustrating Path Analysis for Evaluating Treatment Effect on Change in UACR, after accounting for the treatment effect on change in systolic blood pressure, as further discussed in Example 1.

Because the ANCOVA analysis on UACR was significant for both doses of atrasentan compared with placebo, a path analysis was performed. A set of linear regression models (path analysis) was utilized to evaluate the relationships between change in systolic blood pressure and change in log-transformed UACR (FIG. 5). The results of this analysis showed that atrasentan 0.75 mg had a 97.52% direct effect on change in UACR. This shows that the reduction in blood pressure was not the major contributor to the positive change in UACR.

Figure 6:
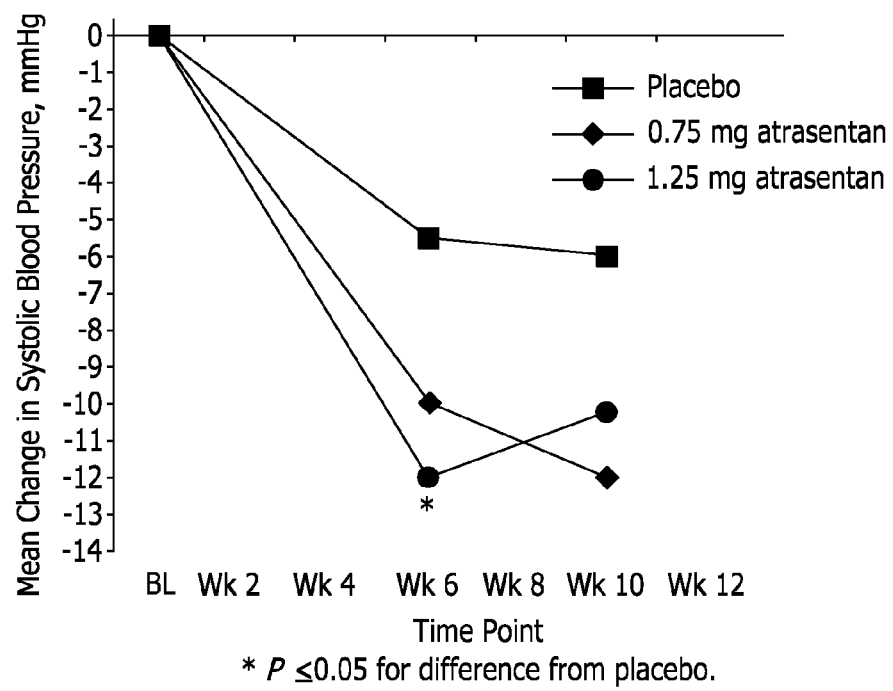
FIG. 6 is a graph illustrating the Mean (Ambulatory) Systolic Blood Pressure Changes from Baseline over time (24 hours), as further discussed in Example 1.

Ambulatory blood pressure was monitored and evaluated at baseline and at Weeks 6 and 10. Mean ambulatory systolic blood pressure decreased from baseline in all groups, with greater mean decreases in the atrasentan treatment groups. The only statistically significant difference was between the 1.25 mg group and placebo at Week 6 (FIG. 6).

Figure 7:
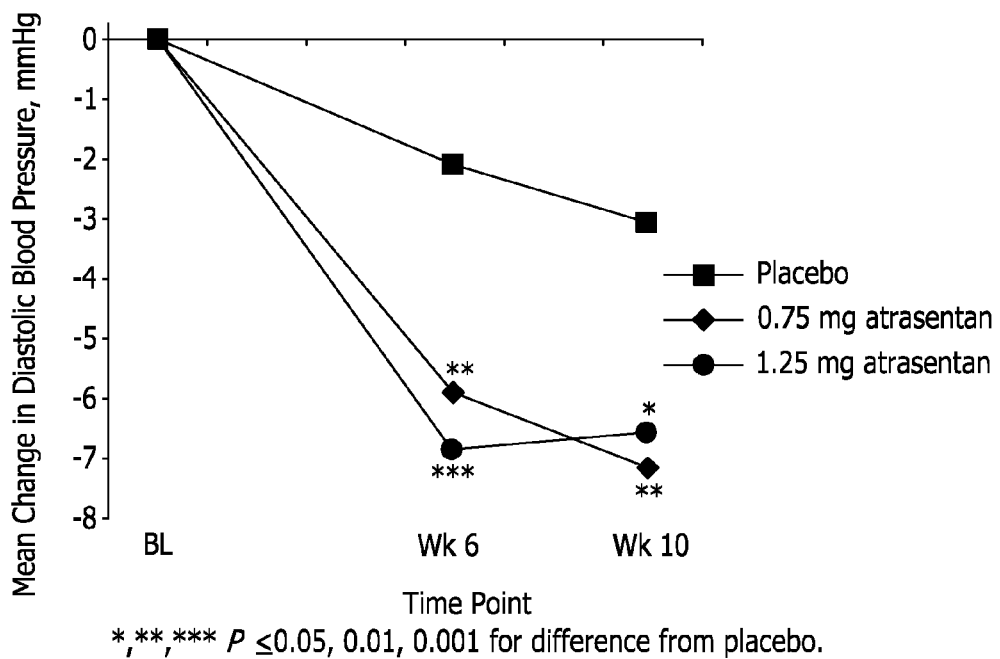
FIG. 7 is a graph illustrating the Mean (Ambulatory) Diastolic Blood Pressure Changes from Baseline over time (24 hours), as further discussed in Example 1.

As with systolic blood pressure, mean ambulatory diastolic blood pressure also decreased from baseline in all groups, with greater mean decreases in the atrasentan treatment groups. The differences between atrasentan and placebo were statistically significant at both time points (FIG. 7).

Figure 8:
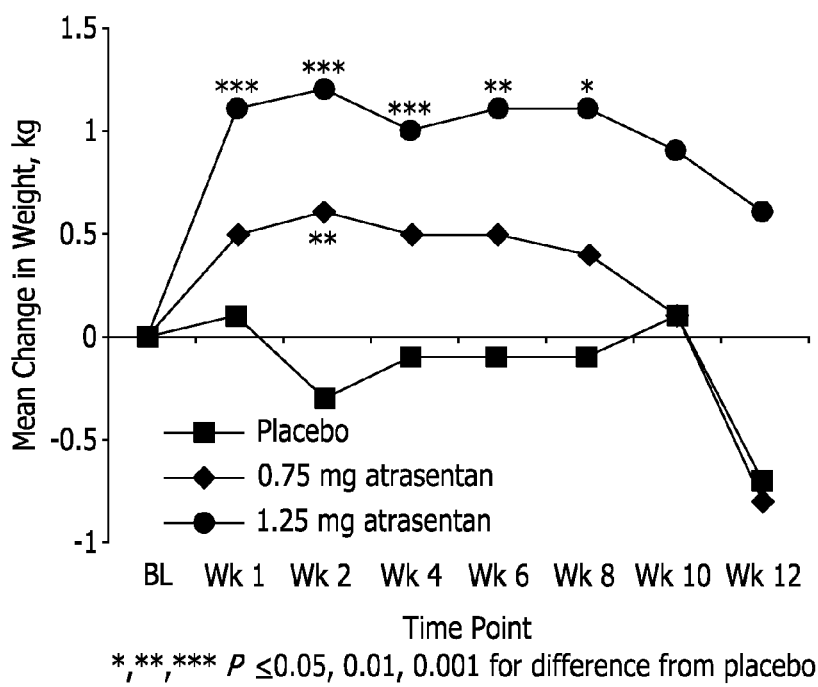
FIG. 8 is a graph illustrating Mean Weight Change from Baseline over time, as further discussed in Example 1.

In repeated-measures analysis of mean changes in weight from baseline over time, the atrasentan 1.25 mg group had statistically significant mean increases at every time point except for Week 12, and the mean increases with atrasentan 1.25 mg were statistically significantly different from the mean changes with placebo from Week 1 through Week 8. For the atrasentan 0.75 mg group, the mean changes from baseline were statistically significant at Weeks 1 and 2 but they were statistically significantly different from placebo only at Week 2 (FIG. 8).

Overall, compared with placebo, both atrasentan groups showed a greater mean decrease from baseline to last on-treatment visit in systolic blood pressure (−2.44 mmHg with 0.75 mg atrasentan and −2.98 mmHg with 1.25 mg atrasentan versus −0.86 mmHg with placebo) and in diastolic blood pressure (−1.49 mmHg with 0.75 atrasentan and −2.74 mmHg with 1.25 mg atrasentan versus −0.62 mmHg with placebo), but the treatment differences were not statistically significant. The 1.25 mg atrasentan group had a mean increase in weight (2.02 kg) compared with mean decreases for both the 0.75 mg group (−1.20 kg) and placebo (−0.97 kg), but the treatment differences were not statistically significant.

All safety analyses were performed on treatment-emergent adverse events only. Treatment-emergent adverse events were defined as those that first occurred or worsened on or after the date of first dose of study drug through 30 days after the last dose of study drug. A higher percentage of subjects in atrasentan 1.25 mg group experienced an adverse event compared with placebo, but the difference was not statistically significant (Table 5).

TABLE 5

Overview of Adverse Events in the Clinical Study of Example 1

| | N (%) of Subjects | | |
| --- | --- | --- | --- |
| | | Atrasentan | |
| Category | Placebo N = 30 | 0.75 mg N = 59 | 1.25 mg N = 64 |
| Any adverse event | 19 (63.3) | 37 (62.7) | 47 (73.4) |
| Possibly or probably drug-related adverse event | 10 (33.3) | 16 (27.1) | 27 (42.2) |
| Severe adverse event | 1 (3.3) | 5 (8.5) | 1 (1.6) |
| Serious adverse event | 3 (10.0) | 4 (6.8) | 4 (6.3) |
| Any adverse event leading to discontinuation of study drug | 0 | 5 (8.5) | 7 (10.9) |
| Fatal adverse event | 0 | 0 | 0 |
| Death | 0 | 0 | 0 |

The most commonly reported adverse events with atrasentan treatment were peripheral edema, constipation, anemia, and fatigue. The incidence of peripheral edema was higher in the placebo group 14 (46.7%) than in either atrasentan group (0.75 mg=19 (32.2%); 1.25 mg=27 (42.2%)), but the differences were not statistically significant. The incidence of anemia was 0 in the placebo group, compared to 4 (6.8%) in the 0.75 mg group and 3 (4.7%) in the 1.25 mg group. The only adverse event with a statistically significant difference between treatment groups was infection, which was reported for 10% of subjects in the placebo group and for 3.4% of subjects in the atrasentan 0.75 mg group and 0% of subjects in the atrasentan 1.25 mg group.

A higher percentage of subjects in the atrasentan groups discontinued study drug because of adverse events (5 subjects (8.5%) with atrasentan 0.75 mg and 7 subjects (10.9%) with atrasentan 1.25 mg) compared with placebo (0 subjects). The adverse events leading to discontinuation for the highest percentage of subjects were peripheral edema (3.4% with atrasentan 0.75 mg and 4.7% with atrasentan 1.25 mg) and fatigue (1.7% with atrasentan 0.75 mg and 3.1% with atrasentan 1.25 mg).

The most common adverse event reported in this study was peripheral edema. While this was not unexpected for atrasentan, the percentage of subjects who experienced peripheral edema was higher in the placebo group (46.7%) compared with the atrasentan groups (32.2% for 0.75 mg and 42.2% for 1.25 mg). At baseline, 68% of the subjects reported no edema. A higher percentage of subjects in the placebo group (43.3%) had mild edema at baseline compared with the 2 atrasentan groups (28.8% and 25.0%). The duration and severity of edema was not statistically significantly different between groups.

The average percentage of days of concomitant diuretic use and the average daily diuretic dose were not statistically significantly different between the 3 treatment groups.

At Week 12, the atrasentan 1.25 mg group had a mean increase in weight of 0.6 kg, compared with a mean decrease of −0.7 kg in the placebo group, but the difference (+1.3 kg) was not statistically significant. The atrasentan 0.75 mg group had a 0.8 kg decrease at Week 12.

Statistically significantly mean decreases in hemoglobin were observed at Week 2 and persisted throughout the study in both atrasentan treatment groups relative to placebo. Finally, no significant differences were found in glucose concentration, from baseline to last on-treatment observation (Table 6). Atrasentan treatment resulted in mean decreases in total cholesterol, low-density lipoprotein cholesterol (LDL-C), and triglycerides compared with mean increases in all 3 variables with placebo. The differences from placebo were statistically significant for cholesterol and LDL-C for both atrasentan groups and for triglycerides for the 1.25 mg group. Mean high-density lipoprotein cholesterol (HDL-C) decreased slightly in all 3 treatment groups, but the change was not clinically meaningful (Table 6).

TABLE 6

Summary of Changes from Baseline to Final On-Treatment Visit in
Variables of Special Interest in Example 1

| Variable/<br>Treatment Group | N | Baseline<br>Mean (SD) | Final On-<br>Treatment<br>Visit Mean<br>(SD) | LS Mean<br>Change from<br>Baseline (SE) | Difference<br>(95% CI) | P Value |
|---|---|---|---|---|---|---|
| Weight, kg[a] | | | | | | |
| Placebo | 28 | 94.8 (18.12) | 92.9 (16.07) | −0.7 (0.92) | | |
| 0.75 mg atrasentan | 51 | 92.8 (21.45) | 93.0 (21.28) | −0.8 (0.69) | −0.1 (−2.32, 2.07) | 0.911 |
| 1.25 mg atrasentan | 55 | 92.7 (17.29) | 92.6 (18.74) | 0.6 (0.66) | 1.3 (−0.88, 3.46) | 0.243 |
| Hemoglobin, g/dL | | | | | | |
| Placebo | 28 | 12.29 (1.616) | 12.26 (1.975) | −0.03 (0.181) | | |
| 0.75 mg atrasentan | 58 | 12.76 (1.299) | 1179 (1.444) | −0.97 (0.126) | −0.94 (−1.423, −0.450) | <0.001 |
| 1.25 mg atrasentan | 64 | 12.81 (1.646) | 11.79 (1.702) | −1.02 (0.120) | −0.98 (−1.462, −0.505) | <0.001 |
| Glucose, mg/dL | | | | | | |
| Placebo | 28 | 168.7 (81.48) | 173.2 (76.70) | 4.5 (15.19) | | |
| 0.75 mg atrasentan | 56 | 162.2 (66.66) | 157.9 (76.55) | −4.3 (10.74) | −8.8 (−49.85, 32.26) | 0.637 |
| 1.25 mg atrasentan | 61 | 162.1 (74.52) | 158.5 (72.59) | −3.7 (10.29) | −8.2 (−48.64, 32.34) | 0.658 |
| Cholesterol, mg/dL | | | | | | |
| Placebo | 28 | 172.5 (48.92) | 173.6 (44.97) | 1.1 (5.30) | | |
| 0.75 mg atrasentan | 51 | 161.8 (38.77) | 148.9 (36.93) | −13.0 (3.93) | −14.1 (−28.65, 0.53) | 0.035 |
| 1.25 mg atrasentan | 56 | 163.8 (37.43) | 147.6 (33.53) | −16.2 (3.75) | −17.2 (−31.60, −2.88) | 0.009 |
| HDL-C, mg/dL | | | | | | |
| Placebo | 28 | 46.2 (12.43) | 43.7 (11.93) | −2.1 (1.42) | | |
| 0.75 mg atrasentan | 51 | 44.3 (12.73) | 42.1 (12.06) | −2.2 (1.05) | 0.2 (−3.68, 4.13) | 0.899 |
| 1.25 mg atrasentan | 56 | 43.6 (10.06) | 43.4 (10.51) | −0.2 (1.00) | 2.2 (−1.61, 6.08) | 0.200 |
| LDL-C, mg/dL | | | | | | |
| Placebo | 26 | 88.5 (38.91) | 90.7 (34.47) | 2.2 (4.00) | | |
| 0.75 mg atrasentan | 46 | 81.7 (31.86) | 71.4 (27.39) | −10.3 (3.01) | −12.5 (−23.56, −1.41) | 0.014 |
| 1.25 mg atrasentan | 52 | 80.4 (27.01) | 69.5 (22.54) | −11.0 (2.83) | −13.1 (−23.98, −2.29) | 0.008 |
| Triglycerides, mg/dL | | | | | | |
| Placebo | 28 | 179.6 (93.74) | 212.9 (190.00) | 33.3 (21.66) | | |
| 0.75 mg atrasentan | 51 | 184.2 (140.97) | 179.9 (101.27) | −4.3 (16.05) | −37.6 (−97.24, 22.01) | 0.165 |
| 1.25 mg atrasentan | 56 | 198.7 (121.57) | 167.4 (84.98) | −31.4 (15.31) | −64.6 (−123.32, −5.97) | 0.016 |

[a]The baseline values were calculated from N = 30 for placebo, N = 59 for atrasentan 0.75 mg, and N = 64 for atrasentan 1.25 mg.
Note:
P value for difference from placebo is from ANOVA with treatment group as a fixed effect for all variables except weight, for which P is from an MMRM analysis.

In conclusion, this example shows that atrasentan 0.75 mg and 1.25 mg once daily resulted in clinically meaningful and statistically significant reduction in albuminuria compared with placebo in type 2 diabetic subjects with nephropathy, who were receiving a maximum tolerated labeled dose of a RAS inhibitor. This positive change in UACR was independent of the known blood pressure-lowering effect of atrasentan. The most common adverse event, peripheral edema, was mild to moderate in severity; no differences in incidence were observed between treatment groups and no difference in the use of diuretics was seen among groups.

Example 2

This example describes a Phase 2b, randomized, double-blind, parallel-design, placebo-controlled, 12-week, multi-center study conducted in Japan to select an effective atrasentan dose for lowering UACR with minimal effect on fluid retention and lowering blood pressure in subjects with type 2 diabetes and nephropathy who are receiving maximum tolerated labeled doses of a RAS inhibitor and a diuretic, unless medically contraindicated. Fifty-eight subjects were randomized (1:1:1) into 3 treatment groups: 1) placebo, 2) atrasentan, 0.75 mg/day, and 2) atrasentan, 1.25 mg/day.

All subjects were Asian. Demographics and baseline characteristics are set forth in Table 7. There were no statistically significant differences between treatment groups in demographics or baseline characteristics, except for the distribution of males and females among treatment groups (P=0.035). The requirement that the subjects be taking a maximum tolerated labeled dose of a RAS inhibitor is reflected in the range of blood pressure at study entry of 132-137/72-75 mmHg. All subjects (100%) were taking diuretics at baseline.

TABLE 7

Demographics and Baseline Characteristics in the Study of Example 2

|  | n (%) of Subjects | | |
| --- | --- | --- | --- |
|  |  | Atrasentan | |
| Variable | Placebo<br>N = 20 | 0.75 mg<br>N = 19 | 1.25 mg<br>N = 19 |
| Sex | | | |
| Female | 2 (10.0) | 5 (26.3) | 9 (47.4) |
| Male | 18 (90.0) | 14 (73.7) | 10 (52.6) |
| Race | | | |
| Asian | 20 (100) | 19 (100) | 19 (100) |
| Age, yr | | | |
| Mean (SD) | 66.4 (9.53) | 67.3 (10.26) | 66.0 (8.10) |
| Weight, kg | | | |
| Mean (SD) | 68.6 (11.0) | 69.3 (12.57) | 73.4 (13.87) |
| BMI, kg/m$^2$ Mean | | | |
| (SD) | 25.9 (3.23) | 27.4 (3.9) | 28.7 (4.83) |
| UACR, mg/g creatinine | | | |
| Mean (SD) | 1570.60 (1204.28) | 1348.88 (1150.58) | 1014.62 (533.08) |
| UACR, log/mg/g creatinine | | | |
| Mean (SD) | 6.99 (0.94) | 6.86 (0.89) | 6.78 (0.58) |
| eGFR, mL/min/BSA | | | |
| Mean (SD) | 53.66 (12.09) | 53.84 (15.05) | 56.92 (16.29) |
| Systolic blood pressure, mmHg | | | |
| Mean (SD) | 132.40 (13.72) | 137.37 (16.58) | 132.76 (15.08) |
| Diastolic blood pressure, mmHg | | | |
| Mean (SD) | 71.93 (9.44) | 75.39 (12.62) | 74.58 (9.51) |

Seven subjects discontinued prematurely from the study. A higher percentage of subjects in the atrasentan groups (10.5% with atrasentan 0.75 mg and 26.3% with atrasentan 1.25 mg) than in the placebo group (0%) discontinued from the study. Six of these subjects discontinued because of an adverse event.

Figure 9:
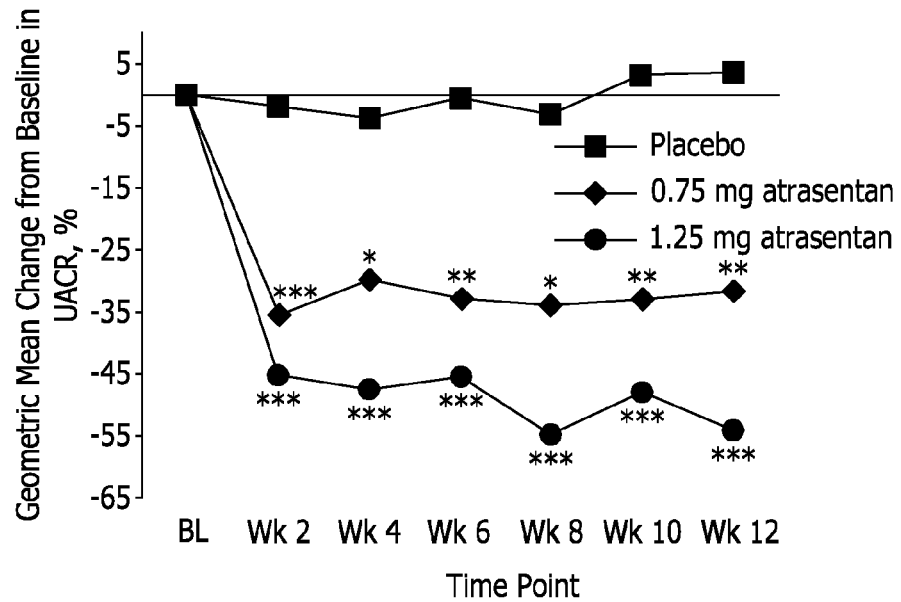
FIG. 9 is a graph illustrating Geometric Mean Change from Baseline in UACR over a 12 week period, as further discussed in Example 2.

The primary efficacy endpoint in this study was the change from Baseline to Week 12 in log-transformed UACR with the primary analysis conducted using MMRM with fixed effects for treatment, visit, and treatment-by-visit interaction, with baseline measurement and baseline-by-visit interaction as covariates. The results showed that both doses of atrasentan resulted in clinically meaningful and statistically significant reductions in UACR relative to placebo at every time point (FIG. 9). Both doses of atrasentan reduced UACR by more than 30% within 2 weeks and this reduction was sustained over 12 weeks of treatment.

Secondary efficacy endpoints in this study included the following analyses: the treatment group differences in change from baseline to final measurement in log-transformed UACR; the treatment group differences in change from baseline to each postbaseline measurement for eGFR; the proportion of subjects who achieve a 30%, 40%, or 50% reduction from baseline to final measurement for UACR; the proportion of subjects who achieve at least 30% reduction from baseline to final measurement for UACR and who have not had a treatment-emergent moderate or severe adverse event edema of any kind (including edema, pulmonary edema, etc.); and the proportion of subjects who have changed from macroalbuminuria (UACR≥300 mg/g) at Baseline to microalbuminuria (UACR<300 mg/g) at final value with at least 20% reduction.

The results of a secondary efficacy analysis on log-transformed UACR of change from baseline to final on-treatment measurement are presented in Table 8. The geometric mean reduction was 31.44% for atrasentan 0.75 mg and 53.76% for atrasentan 1.25 mg compared with a 3.32% mean increase with placebo (P<0.01 for both doses).

TABLE 8

Mean Change from Baseline to Final On-Treatment Measurement in UACR in Example 2

| | | | Change from Baseline | | Between-group Comparison | |
|---|---|---|---|---|---|---|
| Treatment Group | N | Baseline (log mg/g creatinine) | LS Mean (SE) (log mg/g creatinine) | Geometric Mean Change (Percent) | Difference (95% CI) | P Value |
| Placebo | 20 | 6.99 | 0.03 (0.10) | +3.32% | | |
| Atrasentan 0.75 mg | 19 | 6.86 | −0.38 (0.10) | −31.44% | −0.41 (−0.69, −0.13) | 0.005 |
| Atrasentan 1.25 mg | 19 | 6.78 | −0.77 (0.10) | −53.76% | −0.80 (−1.09, −0.52) | <0.001 |

P value is from ANCOVA with treatment and country as main effects and baseline measure as the covariate.

The percentage of subjects who experienced at least a 30% reduction from baseline in log-transformed UACR was statistically significantly different from placebo for both doses of atrasentan. A similarly statistically significantly higher percentage of subjects in both atrasentan groups experienced at least a 40% reduction and a 50% reduction in log-transformed UACR compared with placebo (Table 9).

TABLE 9

Percentage of Subjects with Reduction in Log-Transformed UACR from Baseline to Final Measurement in Example 2

| Treatment Group | N | ≥30% Reduction | | ≥40% Reduction | | ≥50% Reduction | |
|---|---|---|---|---|---|---|---|
| | | Yes | P Value | Yes | P Value | Yes | P Value |
| Placebo | 20 | 10.0% | | 5.0% | | 0% | |
| Atrasentan 0.75 mg | 19 | 52.6% | 0.006 | 31.6% | 0.044 | 21.1% | 0.047 |
| Atrasentan 1.25 mg | 17 | 64.7% | 0.001 | 64.7% | 0.001 | 52.9% | 0.001 |

Note:
P value is for difference from placebo by Fisher's exact test.

The percentage of subjects who experienced at least a 30% reduction in UACR from baseline to the final measurement and who did not have a treatment-emergent moderate or severe adverse event edema was statistically significantly higher in both atrasentan groups compared with placebo (Table 10).

TABLE 10

Percentage of Subjects with 30% Reduction in UACR from Baseline to Final Measurement and with No Moderate or Severe Adverse Event of Edema in Example 2

| Treatment Group | N | Number (%) of Subjects Had ≥30% Reduction in UACR and No Edema | P Value |
|---|---|---|---|
| Placebo | 20 | 2 (10.0) | |
| Atrasentan 0.75 mg | 19 | 8 (42.1) | 0.031 |
| Atrasentan 1.25 mg | 17 | 9 (52.9) | 0.010 |

Note:
P value is for difference from placebo by Fisher's exact test.

Figure 10:
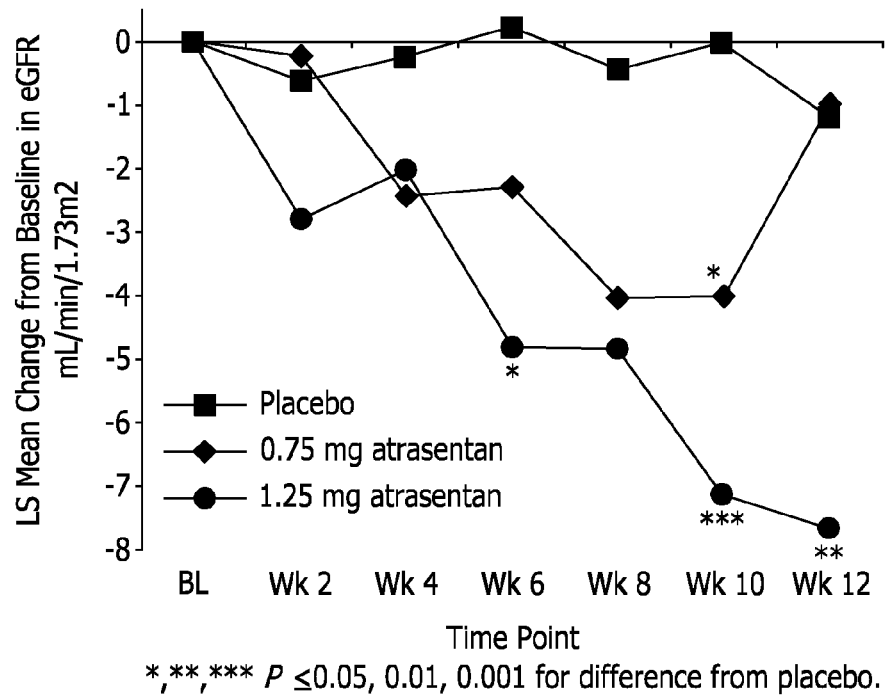
FIG. 10 is a graph illustrating Least Squares (LS) Mean Changes in eGFR from Baseline over time, as further discussed in Example 2.

Mean eGFR decreased from baseline to each postbaseline time point in the atrasentan 1.25 mg group and through Week 10 in the 0.75 mg group. The differences between atrasentan and placebo were statistically significant at Week 10 for the 0.75 mg group and at Weeks 6, 8, and 10 for the 1.25 mg group (FIG. 10).

Figure 11:
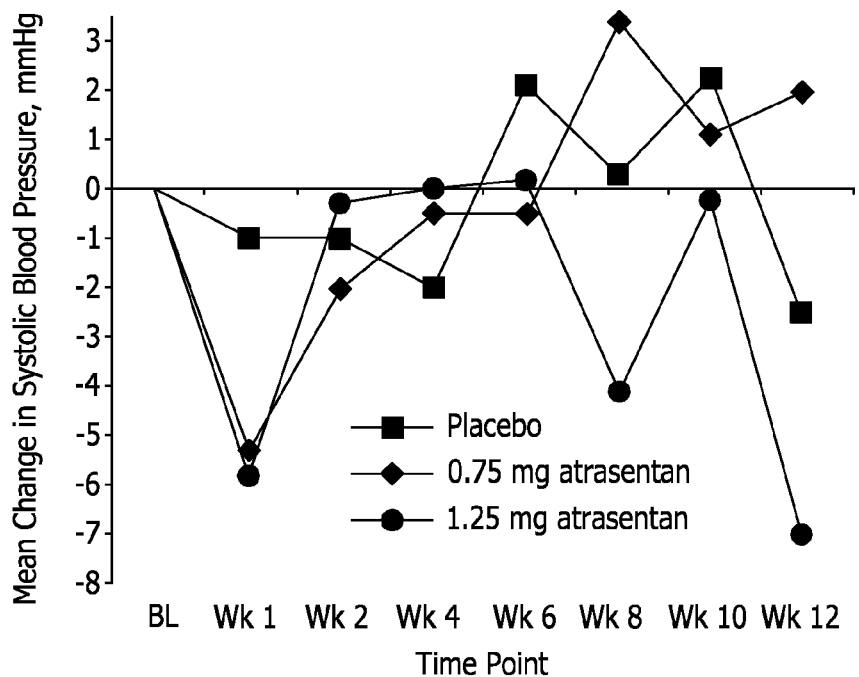
FIG. 11 is a graph illustrating Mean Systolic Blood Pressure Changes from Baseline over time, as further discussed in Example 2.

Mean systolic blood pressure decreased from baseline in all treatment groups at Week 2, and fluctuated over time, with no statistically significant differences between treatment groups (FIG. 11).

Ambulatory blood pressure was monitored and evaluated at baseline and Week 10. Atrasentan treatment resulted in greater mean ambulatory systolic blood pressure decreases from baseline to Week 10 compared with placebo (−5.1 mmHg for atrasentan 0.75 mg and −7.2 mmHg for atrasentan 1.25 mg (P=0.033 for within-group change) compared with −1.2 mmHg for placebo), but the differences between treatments were not statistically significant. Mean (non-ambulatory) systolic blood pressure decreased from baseline to last on-treatment visit in the placebo group (−2.30 mmHg) and the atrasentan 1.25 mg group (−2.93 mmHg), but increased in the 0.75 mg group (1.93 mmHg), with no statistically significant differences between treatment groups.

Figure 12:
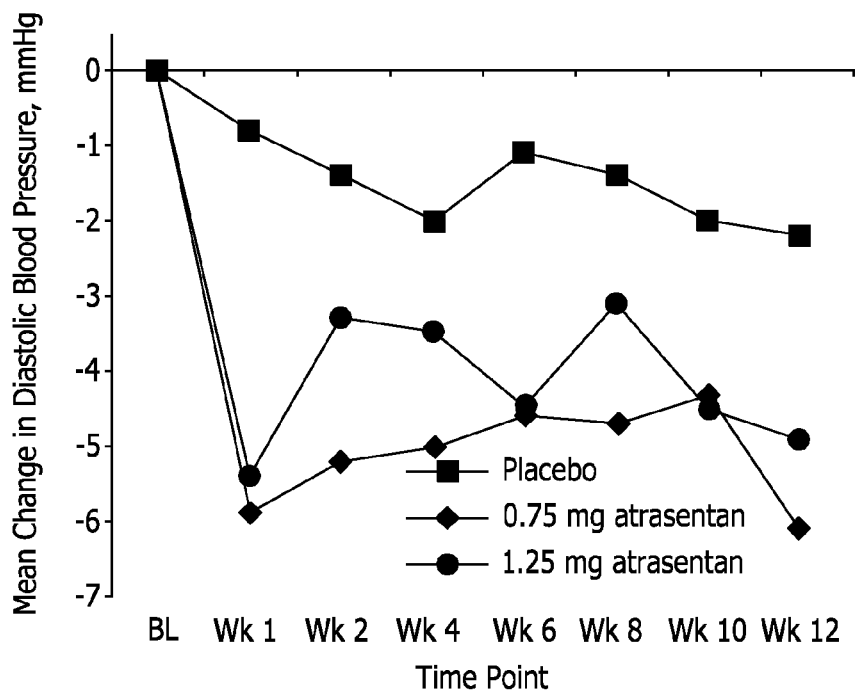
FIG. 12 is a graph illustrating Mean Diastolic Blood Pressure Changes from Baseline over time, as further discussed in Example 2.

Mean diastolic blood pressure decreased from baseline in all treatment groups at Week 2 and with some fluctuation over time, but remained decreased relative to baseline in all 3 groups. The differences between atrasentan and placebo were not statistically significant (FIG. 12).

Mean ambulatory diastolic blood pressure decreased significantly from baseline to Week 10 in both atrasentan groups (P<0.001 for both), and the difference from placebo was also statistically significant as well (−6.0 mmHg for atrasentan 0.75 mg and −6.8 mmHg for atrasentan 1.25 mg compared with −1.5 mmHg for placebo, P<0.05 for both). Mean (non-ambulatory) diastolic blood pressure decreased from baseline to last on-treatment visit in all 3 treatment groups, with greater mean decreases with atrasentan (−5.74 mmHg with 0.75 mg and −4.33 mmHg with 1.25 mg) compared with placebo (−2.19 mmHg), but with no statistically significant differences between treatment groups.

All safety analyses were performed on treatment-emergent adverse events only. Treatment-emergent adverse events were defined as those that first occurred or worsened on or after the date of first dose of study drug through 30 days after the last dose of study drug. A higher percentage of subjects in atrasentan 1.25 mg group experienced an adverse event compared with placebo, but the difference was not statistically significant. (Table 11)

TABLE 11

Overview of Adverse Events in Example 2

| | N (%) of Subjects | | |
|---|---|---|---|
| | | Atrasentan | |
| Category | Placebo N = 20 | 0.75 mg N = 19 | 1.25 mg N = 19 |
| Any adverse event | 14 (70.0) | 17 (89.5) | 14 (73.7) |
| Possibly or probably drug-related adverse event | 8 (40.0) | 7 (36.8) | 10 (52.6) |

TABLE 11-continued

Overview of Adverse Events in Example 2

|  | N (%) of Subjects | | |
|---|---|---|---|
|  |  | Atrasentan | |
| Category | Placebo<br>N = 20 | 0.75 mg<br>N = 19 | 1.25 mg<br>N = 19 |
| Severe adverse event | 0 | 1 (5.3) | 1 (5.3) |
| Serious adverse event | 1 (5.0) | 3 (15.8) | 2 (10.5) |
| Any adverse event leading to discontinuation of study drug | 0 | 1 (5.3) | 5 (26.3)* |
| Fatal adverse event | 0 | 0 | 0 |
| Death | 0 | 0 | 0 |

*$P \leq 0.05$ compared with placebo by Fisher's exact test.

The most commonly reported adverse events with atrasentan treatment were peripheral edema, nasopharyngitis, and anemia. The incidence of peripheral edema was highest in the atrasentan 1.25 mg group (31.6%) compared to 21.1% in the 0.75 mg group and 20.0% in the placebo group, but the difference from placebo was not statistically significant. The difference in incidence was not statistically significant between atrasentan and placebo for any adverse event.

A higher percentage of subjects in the atrasentan groups discontinued study drug because of adverse events (1 subject [5.3%] with atrasentan 0.75 mg and 5 subjects [26.3%] with atrasentan 1.25 mg) compared with placebo (0 subjects). The adverse events leading to discontinuation for the highest percentage of subjects were peripheral edema (3.4% with atrasentan 0.75 mg and 4.7% with atrasentan 1.25 mg) and fatigue (1.7% with atrasentan 0.75 mg and 3.1% with atrasentan 1.25 mg).

All adverse events leading to discontinuation were possibly or probably considered related to study drug, except the event of thyroid cancer.

The most common adverse event reported in this example was peripheral edema. The mean duration of edema was greater in the atrasentan groups (38.2 days for 0.75 mg and 54.8 days for 1.25 mg) than in the placebo group (16.7 days).

The average percentage of days of concomitant diuretic use and the average daily diuretic dose were not statistically significantly different between the 3 treatment groups.

No events of congestive heart failure were reported.

Small mean increases in weight were observed in all 3 treatment groups with no statistically significant differences between atrasentan and placebo at Week 12. The mean increase in weight at Week 12 for the atrasentan 1.25 mg group was 0.4 kg (Table 35).

Statistically significantly mean decreases in hemoglobin were observed at Week 2 and persisted throughout the study in both atrasentan treatment groups relative to placebo. No significant differences were found in glucose concentration, from baseline to final observation (Table 12). Atrasentan treatment resulted in mean decreases in total cholesterol, LDL-C, and triglycerides compared with mean increases in all 3 variables with placebo. The differences from placebo were statistically significant for cholesterol and LDL-C for both atrasentan groups. Mean HDL-C decreased slightly in all 3 treatment groups, but the changes were not clinically meaningful (Table 12).

TABLE 12

Summary of Changes from Baseline to Final On-Treatment Visit in
Variables of Special Interest in Example 2

| Variable/<br>Treatment Group | N | Baseline<br>Mean (SD) | Final<br>On-Treatment<br>Visit Mean<br>(SD) | LS Mean<br>Change<br>from<br>Baseline<br>(SE) | Difference<br>(95% CI) | P Value |
|---|---|---|---|---|---|---|
| Weight, kg[a] | | | | | | |
| Placebo | 20 | 68.6 (11.00) | 68.7 (11.40) | 0.1 (0.43) | | |
| 0.75 mg atrasentan | 18 | 69.3 (12.57) | 69.4 (13.26) | 0.2 (0.45) | 0.1 (−1.13, 1.36) | 0.853 |
| 1.25 mg atrasentan | 14 | 73.4 (13.97) | 74.9 (14.51) | 0.4 (0.49) | 0.4 (−0.96, 1.68) | 0.587 |
| Hemoglobin, g/dL | | | | | | |
| Placebo | 20 | 13.37 (2.036) | 13.11 (2.165) | −1.20 (0.90) | | |
| 0.75 mg atrasentan | 19 | 13.23 (1.816) | 11.74 (1.963) | −3.10 (−0.20) | −1.22 (−1.863, −0.586) | <0.001 |
| 1.25 mg atrasentan | 19 | 13.07 (2.206) | 11.67 (2.300) | −3.80 (0.30) | −1.14 (−1.773, −0.497) | <0.001 |
| Glucose, mg/dL | | | | | | |
| Placebo | 20 | 123.3 (37.10) | 123.1 (32.48) | −0.2 (10.12) | | |
| 0.75 mg atrasentan | 19 | 135.3 (41.55) | 132.1 (37.13) | −3.3 (10.39) | −3.1 (−36.04, 29.92) | 0.834 |
| 1.25 mg atrasentan | 18 | 133.5 (49.25) | 124.3 (33.10) | −9.2 (10.67) | −9.0 (−42.41, 24.48) | 0.545 |
| Cholesterol, mg/dL | | | | | | |
| Placebo | 20 | 196.1 (44.33) | 194.1 (47.25) | −2.0 (5.13) | | |
| 0.75 mg atrasentan | 19 | 201.5 (36.78) | 173.5 (30.52) | −28.0 (5.27) | −26.1 (−42.77, −9.33) | <0.001 |
| 1.25 mg atrasentan | 18 | 196.6 (32.85) | 169.6 (37.60) | −26.9 (5.41) | −25.0 (−41.95, −8.04) | 0.001 |
| HDL-C, mg/dL | | | | | | |
| Placebo | 20 | 48.3 (11.23) | 46.5 (11.59) | −1.8 (1.81) | | |
| 0.75 mg atrasentan | 19 | 51.6 (14.80) | 48.8 (12.65) | −2.8 (1.86) | −1.0 (−6.89, 4.91) | 0.705 |
| 1.25 mg atrasentan | 18 | 50.5 (17.03) | 46.4 (12.12) | −4.1 (1.91) | −2.3 (−8.24, 3.73) | 0.395 |
| LDL-C, mg/dL | | | | | | |
| Placebo | 20 | 115.1 (36.43) | 115.9 (39.19) | 0.8 (4.34) | | |
| 0.75 mg atrasentan | 19 | 113.1 (27.93) | 94.4 (29.10) | −18.6 (4.45) | −19.4 (−33.56, −5.30) | 0.003 |
| 1.25 mg atrasentan | 18 | 110.9 (28.10) | 92.1 (35.00) | −18.9 (4.57) | −19.7 (−34.02, −5.36) | 0.003 |

TABLE 12-continued

Summary of Changes from Baseline to Final On-Treatment Visit in Variables of Special Interest in Example 2

| Variable/<br>Treatment Group | N | Baseline<br>Mean (SD) | Final<br>On-Treatment<br>Visit Mean<br>(SD) | LS Mean<br>Change<br>from<br>Baseline<br>(SE) | Difference<br>(95% CI) | P Value |
|---|---|---|---|---|---|---|
| Triglycerides, mg/dL | | | | | | |
| Placebo | 20 | 143.6 (60.14) | 147.7 (56.03) | 4.1 (51.07) | | |
| 0.75 mg atrasentan | 19 | 176.9 (97.32) | 148.1 (64.63) | −28.8 (50.42) | −32.9 (−74.44, 8.66) | 0.077 |
| 1.25 mg atrasentan | 18 | 173.0 (72.11) | 160.6 (73.37) | −12.4 (68.76) | −16.5 (−58.63, 25.64) | 0.377 |

$^a$The baseline values were calculated from N = 20 for placebo, N = 51 for atrasentan 0.75 mg, and N = 19 for atrasentan 1.25 mg.
Note:
P value for difference from placebo is from ANOVA with treatment group as a fixed effect for all variables except weight, for which P is from an MMRM analysis.

In conclusion, this example shows that atrasentan 0.75 mg and 1.25 mg once daily resulted in clinically meaningful and statistically significant reduction in albuminuria compared with placebo in type 2 diabetic subjects with nephropathy, who were receiving a maximum tolerated labeled dose of a RAS inhibitor. The most common adverse event, peripheral edema, was mild to moderate in severity; no differences in incidence were observed between treatment groups and no difference in the use of diuretics was seen among groups.

Example 3

This example describes a Phase 2b, randomized, double-blind, parallel-design, placebo-controlled, multicenter study to select an effective atrasentan dose for lowering UACR with minimal effect on fluid retention and lowering blood pressure in subjects with type 2 diabetes and nephropathy who are receiving maximum tolerated labeled doses of a RAS inhibitor and a diuretic, unless medically contraindicated. Unlike the previous Phase 2b studies, this example had a shorter treatment period (8 weeks) and evaluated a lower dose of atrasentan (0.5 mg). Forty-eight subjects were randomized (1:1:1) into 3 treatment groups: 1) placebo, 2) atrasentan 0.5 mg/day, and 2) atrasentan 1.25 mg/day. This study also included measurement of thoracic bioimpedance to assess the potential for thoracic fluid retention with atrasentan.

A total of 48 subjects were enrolled into this study, with 16 subjects each in the placebo, atrasentan 0.5 mg, and atrasentan 1.25 mg treatment groups. Demographics and baseline measurements are set forth in Table 13. There was a statistically significant difference between treatment groups in the distribution of subjects by gender; the placebo and atrasentan 0.5 mg groups included a much lower percentage of female subjects than the atrasentan 1.25 mg group (87.5% for both versus 56.3% for 1.25 mg, P=0.012). Subjects in the placebo group had a statistically significantly lower mean age than those in the 2 atrasentan groups (61.8 years, versus 68.5 years for 0.5 mg and 69.4 years for 1.25 mg, P=0.022).

The requirement that the subjects be taking a maximum tolerated labeled dose of a RAS inhibitor is reflected in the range of mean blood pressure at study entry of 138-141/73-77 mmHg. Approximately 92% of the subjects were taking diuretics at baseline (100% in the placebo group, 81.3% in the atrasentan 0.5 mg group, and 93.8% in the atrasentan 1.25 mg group).

TABLE 13

Demographics and Baseline Characteristics in Example 3

| | Number (%) of Subjects | | |
|---|---|---|---|
| | | Atrasentan | |
| Variable | Placebo<br>N = 16 | 0.5 mg<br>N = 16 | 1.25 mg<br>N = 16 |
| Sex | | | |
| Female | 2 (12.5) | 2 (12.5) | 9 (56.3)* |
| Male | 14 (87.5) | 14 (87.5) | 7 (43.8) |
| Race | | | |
| White | 11 (68.8) | 11 (68.0) | 10 (62.5) |
| Black | 4 (25.0) | 4 (25.0) | 3 (18.8) |
| Asian | 0 | 0 | 3 (18.8) |
| Native Hawaiian or other Pacific islander | 1 (6.3) | 0 | 0 |
| Multirace | 0 | 1 (6.3) | 0 |
| Age, yr | | | |
| Mean (SD) | 61.8 (9.20)* | 68.5 (7.92) | 69.4 (7.26) |

TABLE 13-continued

Demographics and Baseline Characteristics in Example 3

| | Number (%) of Subjects | | |
|---|---|---|---|
| | | Atrasentan | |
| Variable | Placebo N = 16 | 0.5 mg N = 16 | 1.25 mg N = 16 |
| Weight, kg | | | |
| Mean (SD) | 99.0 (18.49) | 101.4 (17.23) | 89.7 (22.14) |
| BMI, kg/m$^2$ | | | |
| Mean (SD) | 33.0 (4.60) | 32.8 (4.74) | 32.2 (5.98) |
| UACR, mg/g creatinine | | | |
| Mean (SD) | 1115.81 (855.79) | 1027.48 (835.42) | 1094.47 (878.58) |
| UACR, log/mg/g creatinine | | | |
| Mean (SD) | 6.78 (0.70) | 6.71 (0.67) | 6.71 (0.81) |
| eGFR, mL/min/BSA | | | |
| Mean (SD) | 47.31 (14.54) | 44.69 (13.10) | 41.06 (8.28) |
| Systolic blood pressure, mmHg | | | |
| Mean (SD) | 138.22 (14.97) | 140.44 (15.40) | 141.00 (15.44) |
| Diastolic blood pressure, mmHg | | | |
| Mean (SD) | 77.44 (11.22) | 72.66 (8.85) | 76.16 (9.17) |

*P value ≤ 0.05 for difference between treatment groups by Fisher's exact test for sex and by chi-square for age.

Eight subjects (16.7%) discontinued prematurely from the study. A higher percentage of subjects in the atrasentan groups (12.5% with atrasentan 0.5 mg and 31.3% with atrasentan 1.25 mg) than in the placebo group (6.3%) discontinued from the study. Four subjects overall in the atrasentan groups discontinued because of an adverse event compared with no subject in the placebo group. Abdominal discomfort, fatigue, edema, recurrent prostate cancer, and acute renal failure were the reasons for discontinuation. The differences between treatment groups in the percentage of subjects who discontinued from the study were not statistically significant.

Figure 13:
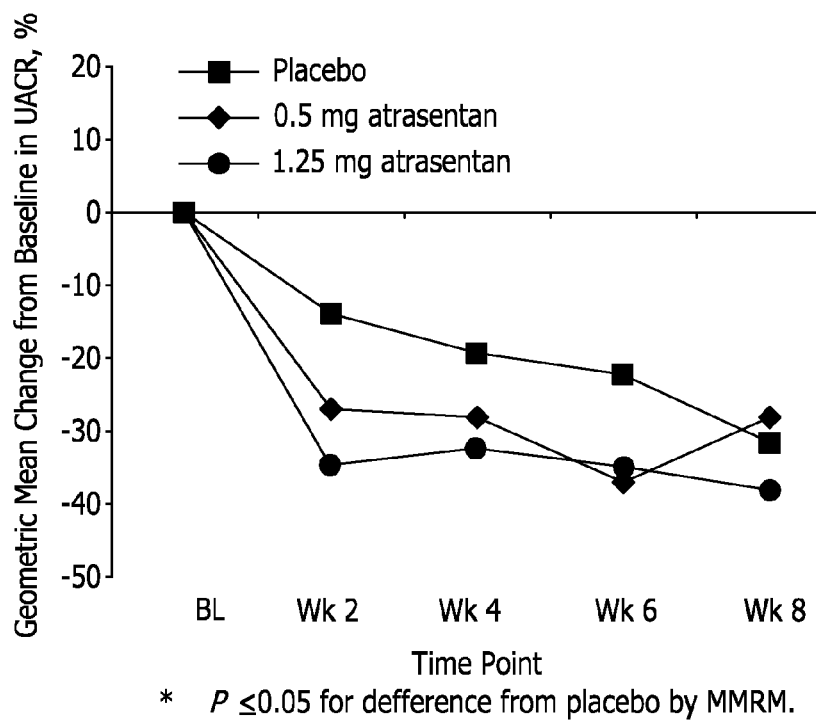
FIG. 13 is a graph illustrating Geometric Mean Change from Baseline in UACR over a 8 week period, as further discussed in Example 3.

The primary efficacy endpoint was the change from baseline to Week 8 in log-transformed UACR with the primary analysis conducted using MMRM with fixed effects for treatment, visit, and treatment-by-visit interaction, with baseline measurement and baseline-by-visit interaction as covariates. The study did not meet the primary endpoint because the treatment differences were not statistically significantly different from placebo (FIG. 13). However, the results showed that both doses of atrasentan resulted in clinically meaningful and statistically significant reductions from baseline in UACR at every time point (FIG. 13). Unlike the results from Example 1 and Example 2, the placebo group in this example showed statistically significant reductions in mean UACR at Week 4, 6, and 8.

Both doses of atrasentan reduced UACR by approximately 30% within 2 weeks and this reduction was sustained over 8 weeks of treatment for the atrasentan 1.25 mg group.

Secondary efficacy endpoints in this study included the following analyses: the treatment group differences in change from baseline to final measurement in log-transformed UACR; the treatment group differences in change from baseline to each postbaseline measurement for eGFR; the proportion of subjects who achieve a 30%, 40%, or 50% reduction from baseline to final measurement for UACR; the proportion of subjects who achieve at least 30% reduction from baseline to final measurement for UACR and who have not had a treatment-emergent moderate or severe adverse event edema of any kind (including edema, pulmonary edema, etc.); and the proportion of subjects who have changed from macroalbuminuria (UACR≥300 mg/g) at Baseline to microalbuminuria (UACR<300 mg/g) at final value with at least 20% reduction.

The results of a secondary efficacy analysis on log-transformed UACR of change from baseline to final on-treatment measurement are presented in Table 14. The geometric mean reduction was 27.7% for atrasentan 0.5 mg and 37.4% for atrasentan 1.25 mg compared with 30.3% with placebo (P>0.05 for both doses).

TABLE 14

Mean Change from Baseline to Final On-Treatment Measurement in UACR in Example 3

| Treatment Group | N | Baseline (log mg/g creatinine) | Change from Baseline LS Mean (SE) (log mg/g creatinine) | Geometric Mean Change (Percent) | Between-group Comparison Difference (90% CI) | P Value |
|---|---|---|---|---|---|---|
| Placebo | 16 | 6.78 | −0.36 | −30.33% | | |
| Atrasentan 0.5 mg | 16 | 6.71 | −0.32 | −27.69% | 0.04 (−0.28, 0.36) | 0.592 |
| Atrasentan 1.25 mg | 16 | 6.71 | −0.47 | −37.45% | −0.11 (−0.43, 0.21) | 0.250 |

Note:
P value is from ANCOVA with treatment and country as main effects and baseline measure as the covariate.

The percentage of subjects who experienced at least a 30%, 40%, or 50% reduction from baseline in log-transformed UACR was not statistically significantly different from placebo for either dose of atrasentan (Table 15).

TABLE 15

Percentage of Subjects with Reduction in Log-Transformed UACR from Baseline to Final Measurement in Example 3

| Treatment Group | N | ≥30% Reduction Yes | P Value | ≥40% Reduction Yes | P Value | ≥50% Reduction Yes | P Value |
|---|---|---|---|---|---|---|---|
| Placebo | 16 | 43.8% | | 43.8% | | 25.0% | |
| Atrasentan 0.5 mg | 16 | 50.0% | 0.999 | 31.3% | 0.716 | 18.8% | 0.999 |
| Atrasentan 1.25 mg | 14 | 42.9% | 0.999 | 42.9% | 0.999 | 35.7% | 0.694 |

Note:
P value is for difference from placebo by Fisher's exact test.

The percentage of subjects who experienced at least a 30% reduction in UACR from baseline to the final measurement and who did not have a treatment-emergent moderate or severe adverse event edema was not statistically significantly different from placebo in either atrasentan group (Table 16).

TABLE 16

Percentage of Subjects with 30% Reduction in UACR from Baseline to Final Measurement and with No Moderate or Severe Adverse Event of Edema in Example 3

| Treatment Group | N | Number (%) of Subjects Had ≥30% Reduction in UACR and No Edema | P Value |
|---|---|---|---|
| Placebo | 16 | 37.5% | |
| Atrasentan 0.5 mg | 16 | 31.3% | 0.999 |
| Atrasentan 1.25 mg | 14 | 28.6% | 0.709 |

Note:
P value is for difference from placebo by Fisher's exact test.

Figure 14:
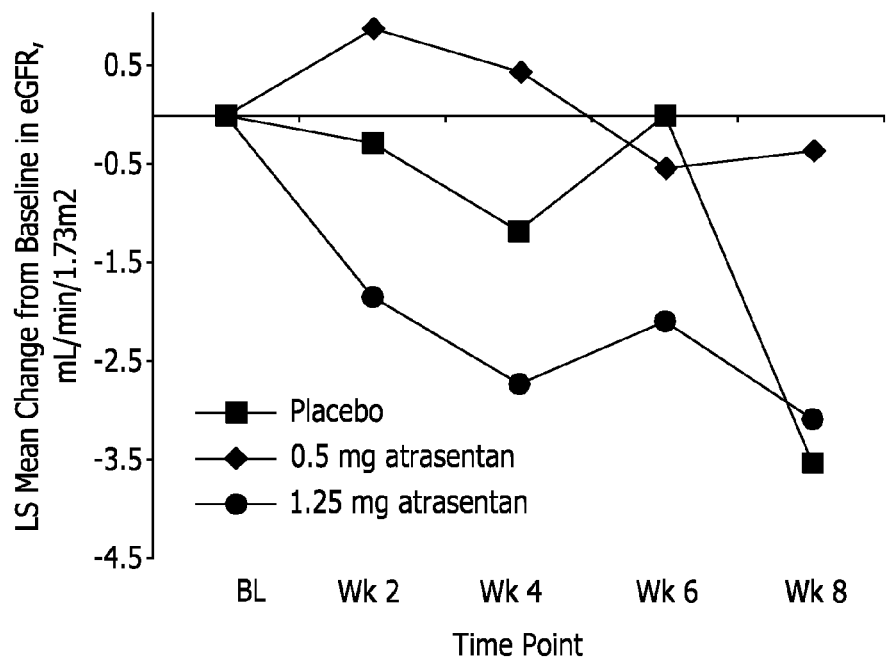
FIG. 14 is a graph illustrating Least Squares (LS) Mean Changes in eGFR from Baseline over time, as further discussed in Example 3.

Mean eGFR decreased from baseline to each postbaseline time point in the atrasentan 1.25 mg group, while it increased at Week 2 and Week 4 for the atrasentan 0.5 mg group. There were no statistically significant differences between placebo and either atrasentan treatment group by repeated-measures analysis (FIG. 14). Subjects in the placebo group experienced a significant decrease in eGFR from baseline to Week 8 (−3.53±1.48 mL/min, P=0.02).

Figure 15:
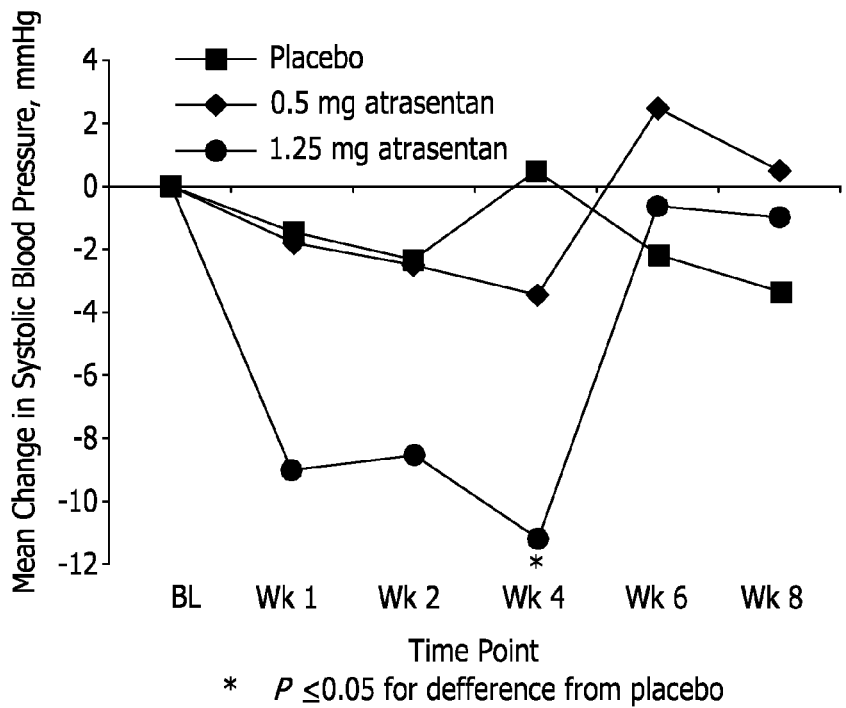
FIG. 15 is a graph illustrating Mean Systolic Blood Pressure Changes from Baseline over time, as further discussed in Example 3.

Mean systolic blood pressure decreased from baseline in all treatment groups at Weeks 1 and 2, with some recovery toward baseline values over time. The difference from baseline for atrasentan 1.25 mg was statistically significant at Weeks 1 and 4, with a statistically significant difference from placebo at Week 4. There were no statistically significant changes from baseline in systolic blood pressure and no statistically significant differences from placebo for the atrasentan 0.5 mg group (FIG. 15).

Figure 16:
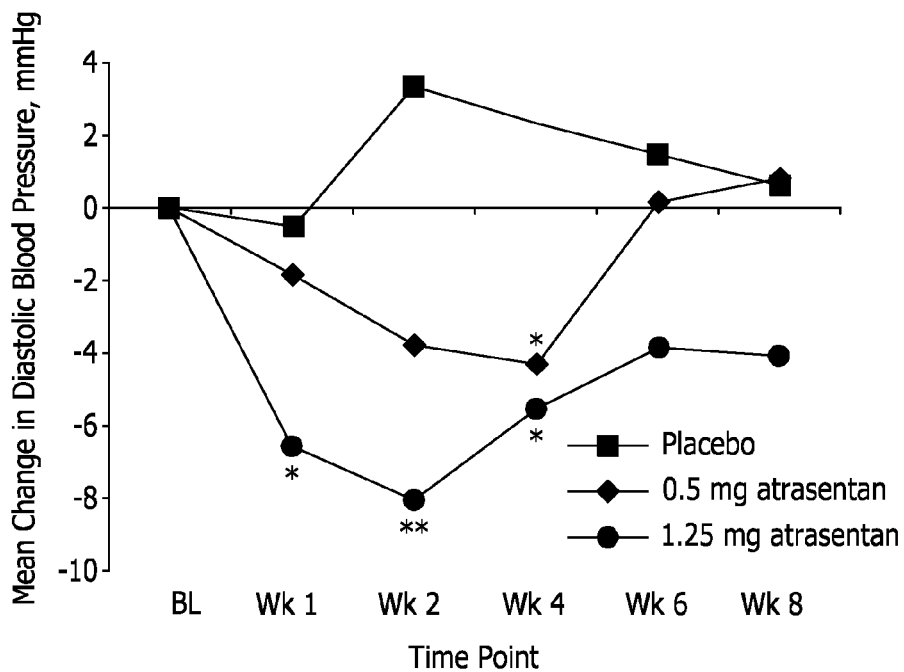
FIG. 16 is a graph illustrating Mean Diastolic Blood Pressure Changes from Baseline over time, as further discussed in Example 3.

Mean diastolic blood pressure decreased from baseline in all treatment groups at Week 1 and then fluctuated over time, with some recovery toward baseline values at Weeks 6 and 8. The difference from baseline and the difference from placebo were statistically significant at Week 4 for atrasentan 0.5 mg. The difference from baseline for atrasentan 1.25 mg was statistically significant from Weeks 1 through 4, with statistically significant differences from placebo at these same time points (FIG. 16).

Because the ANCOVA analysis on UACR was not significant for either dose of atrasentan compared with placebo, the path analysis did not show significant results.

Figure 17:
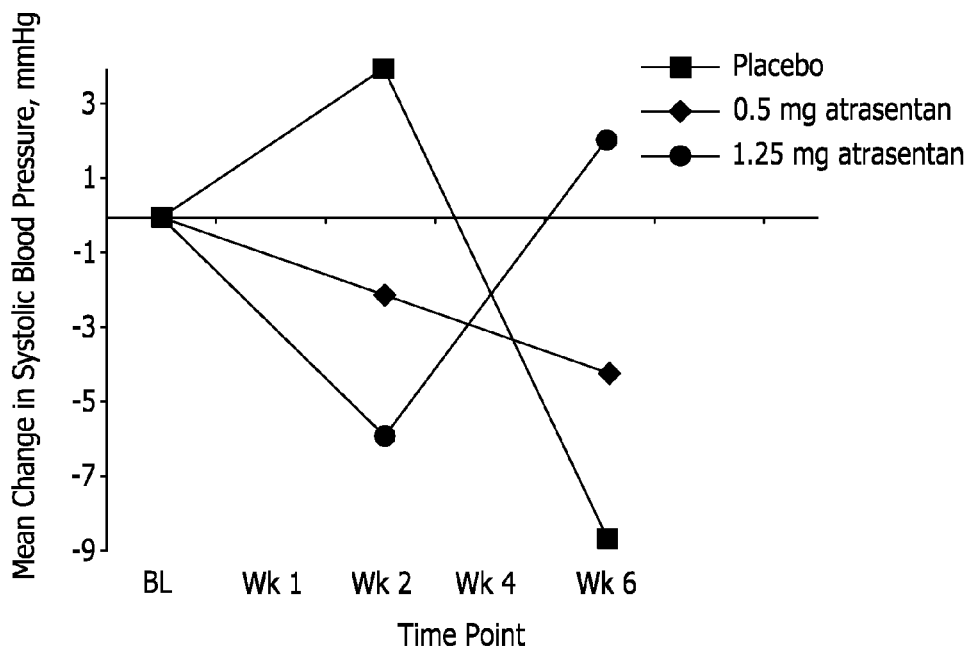
FIG. 17 is a graph illustrating Mean (Ambulatory) Systolic Blood Pressure Changes from Baseline over time (24 hours), as further discussed in Example 3.

Ambulatory blood pressure was monitored and evaluated at baseline and at Weeks 2 and 6. Mean ambulatory systolic blood pressure decreased at Week 2 for the atrasentan 1.25 mg group (nonsignificant decrease), but recovered to slightly above the baseline mean by Week 6. Nonsignificant changes in mean ambulatory systolic blood pressure were observed at both Week 2 and Week 6 for the atrasentan 0.5 mg group; however, none of the differences between atrasentan and placebo were statistically significant. The mean decrease from baseline to Week 6 in the placebo group was statistically significant (P=0.024) (FIG. 17).

Figure 18:
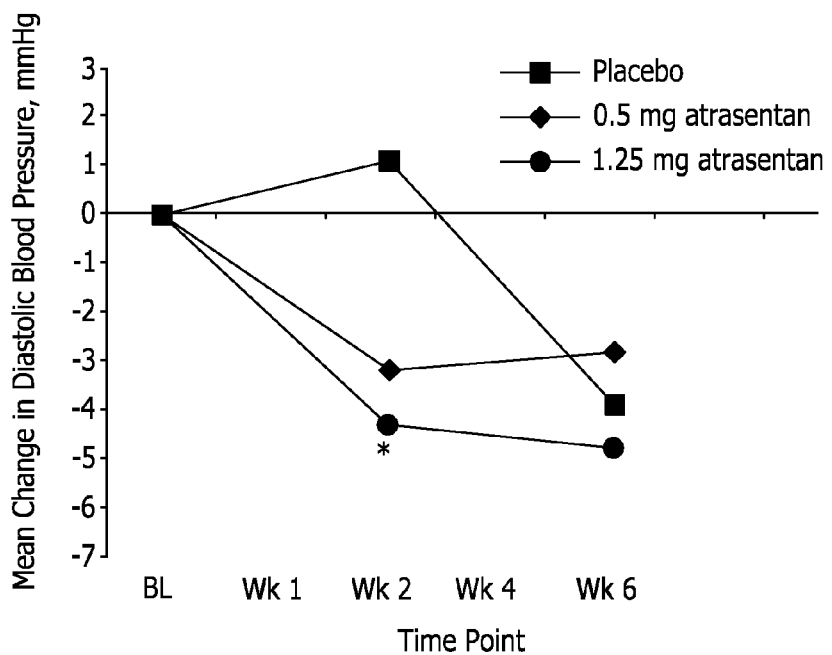
FIG. 18 is a graph illustrating Mean (Ambulatory) Diastolic Blood Pressure Changes from Baseline over time (24 hours), as further discussed in Example 3.

Mean ambulatory diastolic blood pressure decreased from baseline in both atrasentan treatment groups, with greater mean decreases in the atrasentan 1.25 mg group. The differences between atrasentan 1.25 mg and placebo was statistically significant at Week 2 (FIG. 18).

Unlike the results in Examples 1 and 2, the placebo group in this study showed a greater mean decrease from baseline to last on-treatment visit in systolic blood pressure (−3.07 mmHg versus −1.40 mmHg for atrasentan 0.5 mg and +0.85 mmHg for atrasentan 1.25 mg). Both atrasentan groups showed a greater mean decrease in diastolic blood pressure (−4.28 mmHg for 0.5 mg and −0.03 for 1.25 mg) compared with a mean increase for the placebo group (+1.56 mmHg), but the treatment differences were not statistically significant. Both atrasentan groups had a mean increase in weight (+2.58 lb for 0.5 mg and +3.03 kg for 1.25 mg) compared with a small mean decrease in the placebo group (−0.36 lb), but the treatment differences were not statistically significant.

All safety analyses were performed on treatment-emergent adverse events only. Treatment-emergent adverse events were defined as those that first occurred or worsened on or after the date of first dose of study drug through 30 days after the last dose of study drug. An equal percentage of subjects in all 3 groups experienced an adverse event (81.3%). Six subjects (37.5%) in the atrasentan 1.25 mg group experienced a serious adverse event compared with no subject in either the placebo or atrasentan 0.5 mg groups (P=0.018 for difference from placebo). (Table 17).

TABLE 17

Overview of Adverse Events in Example 3

| | N (%) of Subjects | | |
|---|---|---|---|
| | | Atrasentan | |
| Category | Placebo N = 16 | 0.5 mg N = 16 | 1.25 mg N = 16 |
| Any adverse event | 13 (81.3) | 13 (81.3) | 13 (81.3) |
| Possibly or probably drug-related adverse event | 5 (31.3) | 3 (18.8) | 7 (43.8) |
| Severe adverse event | 1 (6.3) | 0 | 2 (12.5) |
| Serious adverse event | 0 | 0 | 6 (37.5)* |
| Any adverse event leading to discontinuation of study drug | 0 | 0 | 3 (18.8) |
| Fatal adverse event | 0 | 0 | 0 |
| Death | 0 | 0 | 0 |

*P ≤ 0.05 for difference from placebo by Fisher's exact test.

The most commonly reported adverse events with atrasentan treatment were peripheral edema, back pain, dyspnea, fatigue, and pneumonia. There were no statistically significant differences between atrasentan and placebo in the incidence of any adverse event preferred term. The incidence of peripheral edema was 7 (43.8%) in the placebo group, 5 (31.3%) in the atrasentan 0.5 mg group, and 8 (50.0%) in the atrasentan 1.25 mg group.

Serious adverse events were experienced by a statistically significantly higher percentage of subjects in the atrasentan 1.25 mg group (37.5%) compared with the placebo group (0 subjects) (P=0.018). No subject in the atrasentan 0.5 mg group experienced a serious adverse event. The only adverse event reported for more than 1 subject was pneumonia (2 subjects, 12.5%).

All of the serious adverse events were considered not related or probably not related to study drug.

Three subjects in the atrasentan 1.25 mg group (18.8%) and no subject in either the atrasentan 0.5 mg group or placebo group experienced an adverse event leading to discontinuation.

Figure 19:
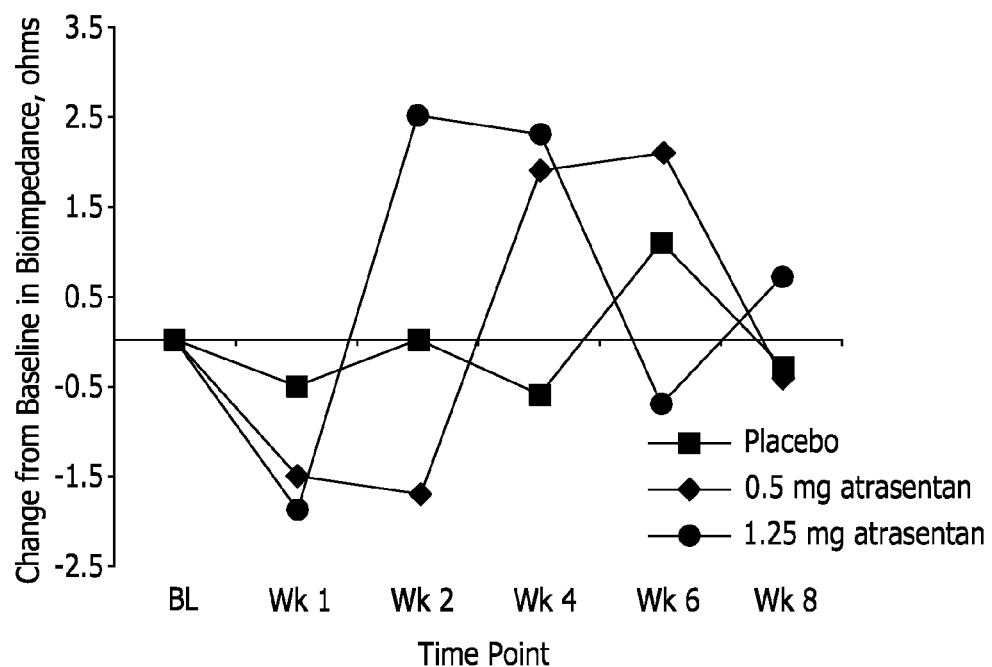
FIG. 19 is a graph illustrating Mean Change from Baseline in Bioimpedance, as further discussed in Example 3.

A mean decrease of 4 ohms in thoracic bioimpedance, as measured by the ZOE® Fluid Status Monitor, is considered clinically indicative of thoracic fluid overload. Mean thoracic bioimpedance fluctuated in all treatment groups over time, with greater mean changes in the 2 atrasentan groups than in the placebo group. None of the groups exhibited mean changes greater than 2.5 ohms at any time point (FIG. 19). Importantly, there were no statistically significant differences between the atrasentan treatment group and the placebo, indicating no negative effect of fluid retention caused by atrasentan in this population.

The most common adverse event reported in this study was peripheral edema. The percentage of subjects who experienced peripheral edema was 43.8% in the placebo group, 31.3% in the atrasentan 0.5 mg group, and 50.0% in the atrasentan 1.25 mg group. At baseline, 54.2% of the subjects reported no edema. An equal percentage of subjects in all 3 groups had mild edema at baseline (43.8%).

The duration and severity of edema was not statistically significantly different between groups.

During the study, subjects in the placebo group were taking a statistically significantly higher average daily dose of thiazide diuretics (25 mg versus 17.5 mg for atrasentan 0.5 mg and 15.6 mg for atrasentan 1.25 mg; P=0.026) and for a longer average duration compared with subjects in the 2 atrasentan treatment groups (97 days versus 90 days for atrasentan 0.5 mg and 79 days for atrasentan 1.25 mg).

One subject experienced congestive heart failure. The subject experienced the event 7 days after the last dose atrasentan 1.25 mg, concurrently with an event of pulmonary hypertension. The investigator considered the congestive heart failure probably not related to study drug and provided an alternative etiology of significant coronary artery disease with 80% to 90% stenosis of the left anterior descending coronary artery. Four days later, the subject experienced an event of coronary artery stenosis, which the investigator considered not related to study drug, but to existing hyperlipidemia.

At Week 8, the atrasentan 1.25 mg group had a mean increase in weight of 0.8 kg, compared with a mean decrease of −0.1 kg in the placebo group, but the difference (+0.8 kg) was not statistically significant. Similarly, the atrasentan 0.5 mg group had a mean increase in weight of 1.3 kg, compared with a mean decrease of −0.1 kg in the placebo group, but the difference (+1.4 kg) was also not statistically significant.

Statistically significantly mean decreases in hemoglobin were observed at Week 2 and persisted throughout the study for the atrasentan 1.25 mg group relative to placebo. The differences in mean decreases in hemoglobin were statistically significantly different from placebo in the atrasentan 0.5 mg group at Weeks 4 and 6. No significant differences were found in glucose concentration, from baseline to final on-treatment measurement (Table 18).

Atrasentan 1.25 mg treatment resulted in greater mean decreases in total cholesterol, LDL-C, and triglycerides compared with smaller mean decreases in total cholesterol and LDL-C and a mean increase in triglycerides for placebo.

TABLE 18

Summary of Changes from Baseline to Final On-Treatment Visit in Variables of Special Interest in Example 3

| Variable/Treatment Group | N | Baseline Mean (SD) | Final On-Treatment Visit Mean (SD) | LS Mean Change from Baseline (SE) | Difference (95% CI) | P Value |
|---|---|---|---|---|---|---|
| Weight, kg$^a$ | | | | | | |
| Placebo | 15 | 99.0 (18.49) | 98.9 (19.19) | −0.1 (0.73) | | |
| 0.5 mg atrasentan | 14 | 101.4 (17.23) | 101.1 (18.50) | 1.3 (0.74) | 1.4 (−0.70, 3.47) | 0.188 |
| 1.25 mg atrasentan | 11 | 89.7 (22.14) | 85.3 (22.88) | 0.8 (0.81) | 0.8 (−1.39, 3.07) | 0.452 |

TABLE 18-continued

Summary of Changes from Baseline to Final On-Treatment Visit in Variables of Special Interest in Example 3

| Variable/Treatment Group | N | Baseline Mean (SD) | Final On-Treatment Visit Mean (SD) | LS Mean Change from Baseline (SE) | Difference (95% CI) | P Value |
|---|---|---|---|---|---|---|
| Hemoglobin, g/dL | | | | | | |
| Placebo | 16 | 13.53 (1.619) | 13.26 (1.734) | −0.28 (0.198) | | |
| 0.5 mg atrasentan | 16 | 13.34 (1.732) | 12.53 (1.964) | −0.82 (0.198) | −0.54 (−1.184, 0.097) | 0.059 |
| 1.25 mg atrasentan | 16 | 12.44 (1.260) | 11.29 (1.573) | −1.16 (0.198) | −0.88 (−1.522, −0.241) | 0.003 |
| Glucose, mg/dL | | | | | | |
| Placebo | 16 | 156.0 (51.12) | 168.1 (97.47) | 12.1 (18.06) | | |
| 0.5 mg atrasentan | 16 | 155.4 (62.13) | 181.4 (62.96) | 26.0 (18.06) | 13.9 (−44.46, 72.34) | 0.58 |
| 1.25 mg atrasentan | 15 | 155.0 (47.76) | 179.9 (65.51) | 24.9 (18.65) | 12.9 (−46.49, 752.23) | 0.623 |
| Cholesterol, mg/dL | | | | | | |
| Placebo | 15 | 183.9 (36.22) | 178.8 (43.67) | −5.1 (7.05) | | |
| 0.5 mg atrasentan | 15 | 156.7 (38.81) | 155.1 (40.36) | −1.5 (7.05) | 3.6 (−19.26, 26.46) | 0.720 |
| 1.25 mg atrasentan | 14 | 189.2 (46.40) | 169.4 (46.02) | −19.9 (7.30) | −14.7 (−37.99, 8.54) | 0.155 |
| HDL-C, mg/dL | | | | | | |
| Placebo | 15 | 41.6 (9.03) | 39.3 (10.36) | −2.3 (1.67) | | |
| 0.5 mg atrasentan | 15 | 41.5 (9.72) | 41.1 (9.92) | −0.5 (1.67) | 1.9 (−3.54, 7.28) | 0.434 |
| 1.25 mg atrasentan | 14 | 57.6 (19.51) | 53.9 (22.23) | −3.7 (1.73) | −1.4 (−6.89, 4.13) | 0.569 |
| LDL-C, mg/dL | | | | | | |
| Placebo | 12 | 89.3 (22.33) | 85.9 (30.65) | −3.4 (7.21) | | |
| 0.5 mg atrasentan | 14 | 68.4 (20.92) | 68.1 (23.33) | −0.3 (6.67) | 3.1 (−19.49, 25.75) | 0.752 |
| 1.25 mg atrasentan | 12 | 92.2 (49.40) | 78.9 (37.01) | −13.3 (7.21) | −9.8 (−33.30, 13.64) | 0.341 |
| Triglycerides, mg/dL | | | | | | |
| Placebo | 15 | 265.9 (172.52) | 293.4 (230.47) | 27.5 (22.89) | | |
| 0.5 mg atrasentan | 15 | 208.4 (87.70) | 206.1 (71.42) | −2.3 (22.89) | −29.8 (−14.09, 44.49) | 0.363 |
| 1.25 mg atrasentan | 13 | 190.5 (92.63) | 187.1 (115.90) | −3.5 (24.59) | −31.0 (−108.09, 46.10) | 0.362 |

[a]The baseline values were calculated from N = 16 for placebo, N = 16 for atrasentan 0.5 mg, and N = 16 for atrasentan 1.25 mg.
Note:
P value for difference from placebo is from ANOVA with treatment group as a fixed effect for all variables except weight, for which P is from an MMRM analysis.

In conclusion, this example demonstrates that atrasentan 0.5 mg and 1.25 mg resulted in no significant difference in thoracic bioimpedance compared with placebo. The magnitude of UACR reduction in the atrasentan groups was similar to that in the previous two Phase 2b studies (Examples 1 and 2), although both primary and secondary efficacy endpoints did not reach statistical significance because of an unexpected effect in the placebo group. The lowest dose of atrasentan (0.5 mg) did not have an effect in blood pressure. Mild to moderate and clinically tolerable peripheral edema was the most commonly reported adverse event, although no significant difference among groups was found. The greater use of diuretics in the placebo group might explain some of the changes observed in UACR, systolic blood pressure, and eGFR with placebo.

This example also demonstrates the unpredictability of a given dosage form of atrasentan with respect to both efficacy in terms of reduction in UACR and safety in terms of peripheral edema. While Examples 1 and 2 demonstrated a reduction in UACR for a dose of 1.25 mg per day, this example did not yield a statistically significant reduction. A dose of 0.5 mg atrasentan HCl was not demonstrated to result in a statistically significant reduction in UACR, lending to unpredictability as to the efficacy of dose amounts of atrasentan greater than 0.5 mg and less than 0.75 mg.

Example 4

A review of the data obtained from the studies detailed in Examples 1 and 2, above, with respect to total serum cholesterol and serum LDL cholesterol, indicated a meaningful reduction was achieved relative to baseline for both. For example, although the reduction in total serum cholesterol and serum LDL cholesterol for subjects receiving a 0.75 mg dose of atrasentan, after 12 weeks of therapy, varied, the average for both of the studies detailed in Examples 1 and 2 was approximately 14%.

As a result, the data obtained from these studies as further reviewed subsequent to collection and a sub-population of subjects in each study was identified as receiving or taking a statin in combination with the atrasentan dose (either a 0.75 mg or 1.25 mg dose). The data relating to the impact of atrasentan on total serum cholesterol and serum LDL cholesterol from each study for this sub-population was combined and a new average (mean) baseline, as well as change relative thereto over the time period of the study, was calculated for each of the total serum cholesterol and serum LDL cholesterol. For purposes of comparison, data relating to the impact of atrasentan on total serum cholesterol and serum LDL cholesterol for each study for subjects that were not receiving or taking a statin was combined and a new average (mean) baseline, as well as change relative thereto over the time period of the study, was also calculated for each of the total serum cholesterol and serum LDL cholesterol. The results are reported in the Table 19, below.

TABLE 19

Changes from Baseline for Sub-population of Subjects Receiving Statins from Studies of Examples 1 and 2.

| Variable | Treatment Group | N | Treatment | N | Mean Baseline (SD) | Mean Change (SD) | % Change |
|---|---|---|---|---|---|---|---|
| Total C | Statin | 161 | | | | | |
| | | | Placebo | 38 | 180.7 (51.1) | −0.5 (29.0) | −0.3 |
| | | | 0.75 mg Atrasentan | 57 | 165.4 (41.9) | −17.1 (28.4) | −10.4 |
| | | | 1.25 mg Atrasentan | 66 | 164.4 (34.5) | −17.1 (28.0) | −10.4 |
| | Non-Statin | 49 | Placebo | 12 | 190.7 (36.0) | 0.8 (23.0) | 0.4 |
| | | | 0.75 mg Atrasentan | 21 | 179.0 (42.0) | −14.9 (5.7) | −9.3 |
| | | | 1.25 mg Atrasentan | 16 | 201.0 (37.8) | −18.4 (6.5) | −12.8 |
| LDL | Statin | 154 | | | | | |
| | | | Placebo | 37 | 96.9 (41.6) | 2.4 (20.5) | 2.5 |
| | | | 0.75 mg Atrasentan | 54 | 82.7 (33.2) | −12.8 (20.2) | −15.4 |
| | | | 1.25 mg Atrasentan | 63 | 81.9 (26.1) | −11.6 (17.8) | −14.2 |
| | Non-Statin | 47 | Placebo | 12 | 111.7 (27.4) | −0.8 (18.7) | −0.7 |
| | | | 0.75 mg Atrasentan | 21 | 101.8 (31.2) | −13.4 (18.9) | −13.1 |
| | | | 1.25 mg Atrasentan | 16 | 111.8 (33.3) | −21.0 (31.0) | −18.8 |

The results reported in Table X indicate that those subjects receiving statins and 0.75 mg of atrasentan experienced a 15% reduction in LDL cholesterol and 10% reduction in total cholesterol. Similar results were observed in those subjects that were not receiving statins (13% and 9% reduction, respectively). These results suggest that the association seen between atrasentan and reduction in lipids is independent of the use of statins.

Example 5

In the example, a preclinical animal model is used to evaluate whether atrasentan and an ARB cause a synergistic hypotensive effect.

Such a synergistic hypotensive effect would be expected and predicted based upon the prior art, such as Mohanan et al., TRC120038, a Novel Dual AT(1)/ET(A) Receptor Blocker for Control of Hypertension, Diabetic Nephropathy, and Cardiomyopathy in ob-ZSF1 Rats. International Journal of Hypertension, vol. 2011, Article ID 751513, 12 pages, 2011. Mohanan et al. note that in hypertensive subjects, angiotensin II and endothelin participate in a manner involving closely interwoven pathways in increasing blood pressure (BP) and inducing end organ damage. In this model of diabetic nephropathy (type 2 diabetes) using obese Zucker hypertensive fatty rats (ob-ZSF1), the ARB candesartan produced a significant decrease in mean blood pressure. TRC120038 is a dual acting antagonist, inhibiting both angiotensin II receptor (AT1) & endothelin receptor A. In the ob-ZSF1 model, the dual antagonist TRC120038 produced a more profound decrease in mean blood pressure, demonstrating a synergistic hypotensive effect of combining the ARB/ET-A mechanisms.

This synergistic hypotensive effect was demonstrated in a clinical study where the endothelin receptor A antagonist BQ-123 was administered in combination with the ACE inhibitor enalapril. Goddard et al., Endothelin A receptor antagonism and angiotensin-converting enzyme inhibition are synergistic via an endothelin B receptor-mediated and nitric oxide-dependent mechanism. J Am Soc Nephrol. 15(10):2601-10 (2004). Mean arterial pressure was reduced by BQ-123, an effect that was doubled during ACE inhibition. The mean area under curve+/−SEM for BQ-123 alone was −2.3 mmHg+/−1.8%, and for BQ-123 plus enalapril, it was −5.1 mmHg+/−1.1%, with P<0.05 versus placebo.

A preclinical study was conducted to determine whether atrasentan would exhibit a synergistic hypotensive effect when administered in combination with an ARB. An ARB, losartan (10 mg/kg/day), was administered for 12 weeks, to ob-ZSF1 rats (the same model used by Mohanan et al.), and a significant decrease in mean arterial pressure (MAP) was observed. Atrasentan alone at 1.5 mg/kg/day or 5 mg/kg/day did not significantly affect mean arterial pressure. When atrasentan (1.5 mg/kg/day) was combined with losartan (10 mg/kg/day), the decrease in MAP produced was approximately the same as the decrease in MAP when losartan was administered alone. Accordingly, this preclinical study demonstrated that there is no hypotensive synergism between atrasentan and losartan.

Example 6

Figure 20:
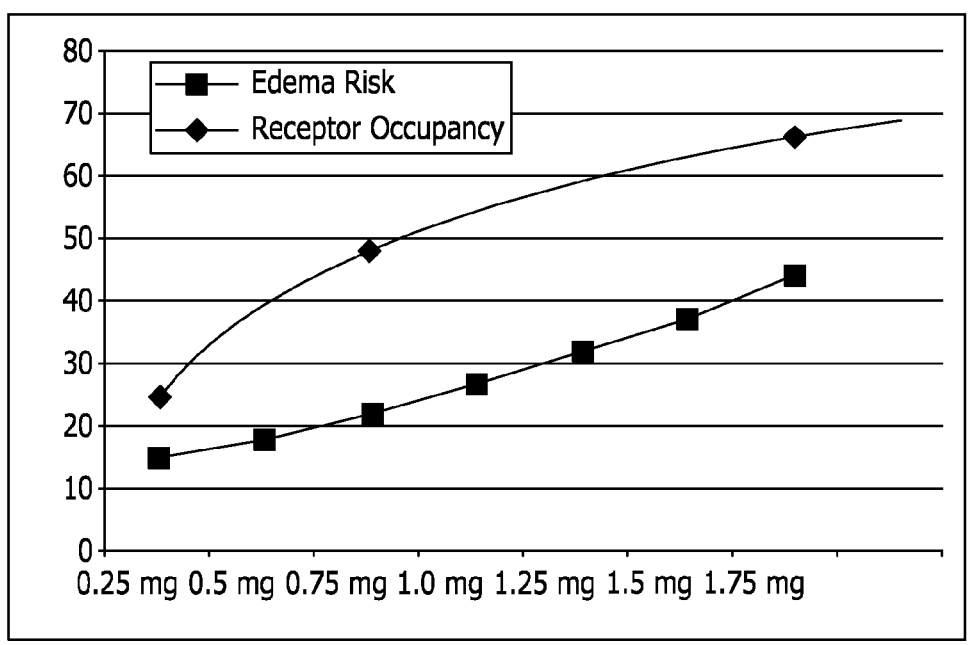
FIG. 20 is a graph illustrating Modeling Data on Edema Rish and Receptor Occupancy, as further discussed in Example 6.

FIG. 20 shows a graph that uses modeling data on edema risk (dark squares) developed by statistical analysis based on a Phase 2A study only (NCT00920764). The graph was made by overlaying receptor occupancy data. (See also Table 20, below.)

If edema were caused by off-target activity against ETBR at high doses, then one would expect to see the edema risk only start to pick up at higher doses. Instead it rises proportionally across the ETAR receptor occupancy curve. In Kohan, et al., Addition of Atrasentan to Renin-Angiotensin System Blockade Reduces Albuminuria in Diabetic Nephropathy. J. Am Soc Nephrol 22:763-72 (2011), the authors conclude that a selective ETAR (atrasentan) may avoid edema seen with less selective endothelin antagonists. However, this theory does not appear to be supported by the data reported in that same 2011 paper.

TABLE 20

| Dose | Risk of edema | Receptor Occupancy |
|---|---|---|
| 0.25 mg | 15% | 25% |
| 0.75 mg | 22% | 47% |
| 1.75 mg | 43% | 67% |

Example 7

The data collected in the Phase IIb studies discussed in Examples 1 and 2 above were pooled and further analyzed for the combined subject population (N=211).

FIG. 21 is a summary of the demographic information for the combined subject population including the demographic information for each of the three treatment groups (i.e., the placebo (N=50), atrasentan 0.75 mg (N=78), and atrasentan 1.25 mg (N=83) treatment groups).

Figure 22:
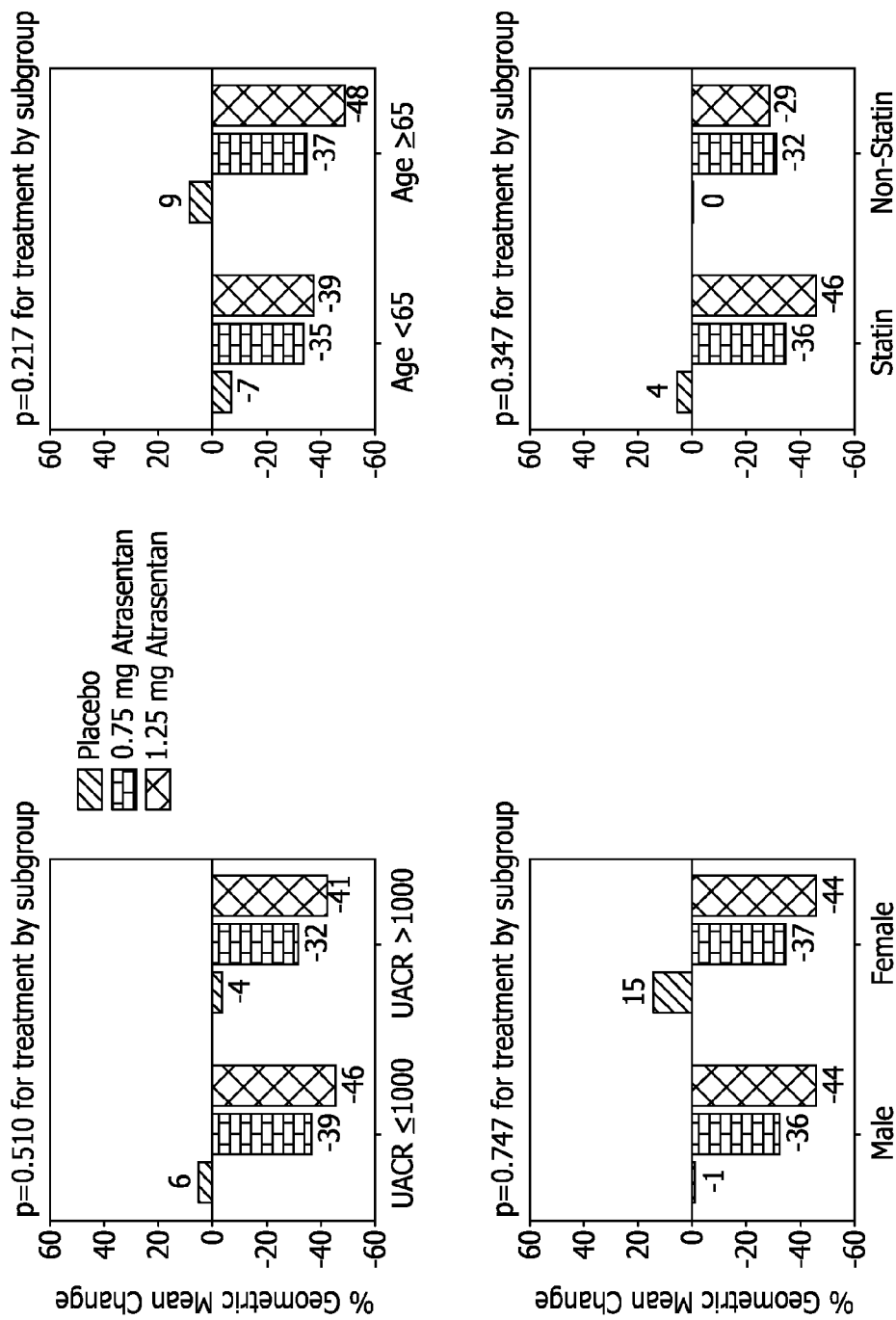
FIG. 22 is a bar chart depiction of the percent geometric mean change in UACR for the following subgroups within the combined subject population: (a) UACR≤1000 mg/g vs. UACR≥1000 mg/g, (b) male vs. female, (c) age <65 vs. age ≥65, and (d) concurrent treatment with a statin vs. no concurrent treatment with a statin, as discussed in Example 7.

FIG. 22 comprises bar chart depictions of the percent geometric mean change in UACR for the following subgroups within the combined subject population: (a) UACR≤1000 mg/g vs. UACR≥1000 mg/g, (b) male vs. female, (c) age <65 vs. age ≥65, and (d) concurrent treatment with a statin vs. no concurrent treatment with a statin.

Figure 23:
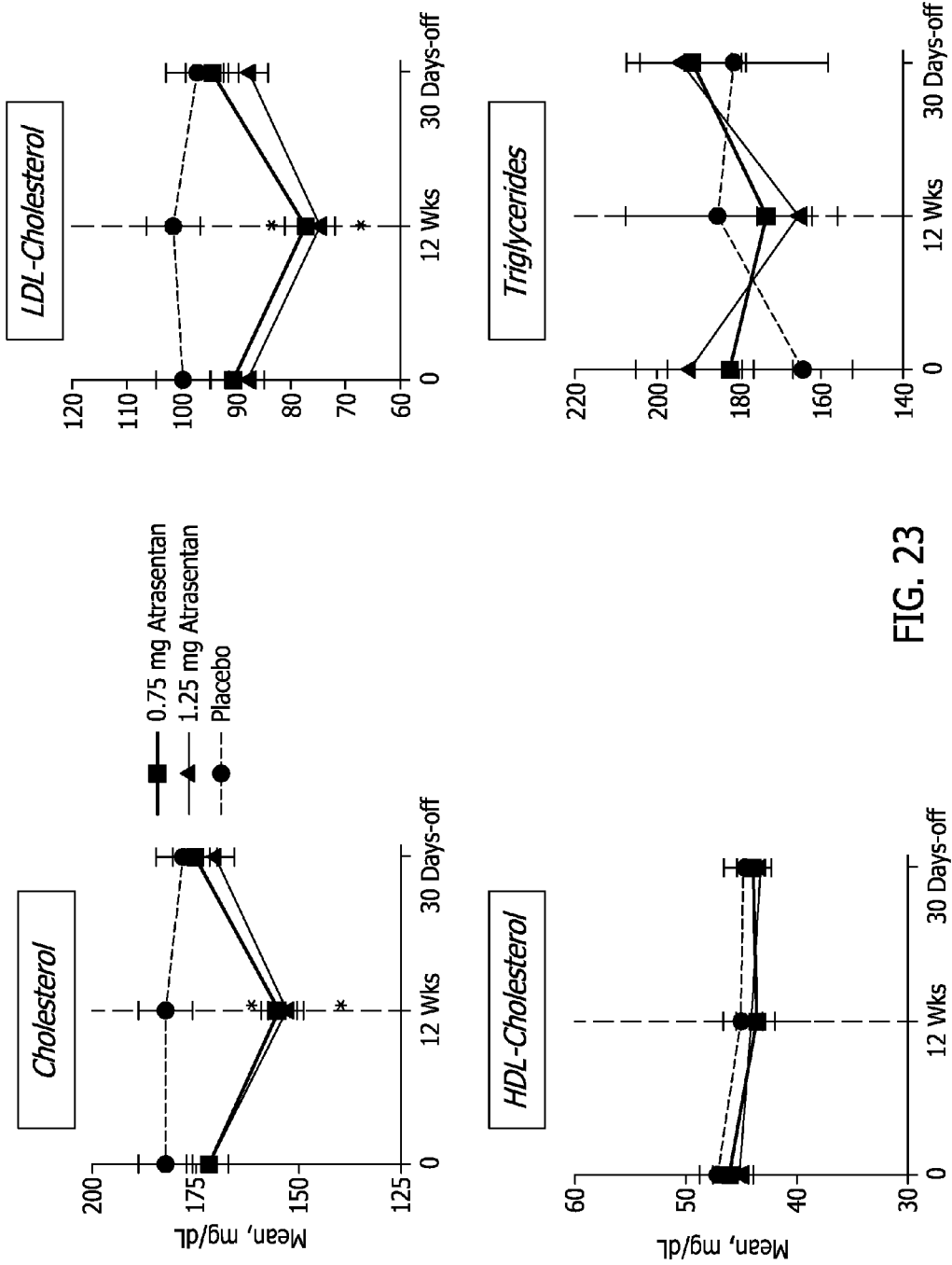
FIG. 23 comprises graphical depictions of the mean total cholesterol, mean LDL cholesterol, mean HDL cholesterol, and mean triglyceride values (mg/dL) for the combined subject population over the 12-week treatment period plus a 30-day period after discontinuation of treatment, as discussed in Example 7.

FIG. 23 comprises graphical depictions of the mean total cholesterol, mean LDL cholesterol, mean HDL cholesterol, and mean triglyceride values (mg/dL) for the combined subject population over the 12-week treatment period plus a 30-day period after discontinuation of treatment.

This written description uses examples to disclose and illustrate certain embodiments, including the best mode, and also to enable any person skilled in the art to practice such embodiments. Patentable scope is defined by the claims, and may include other examples or subject matter that occurs to those skilled in the art. Such other examples or subject matter are intended to be within the scope of the claims if they have structural elements that do not differ from the literal language of the claims, or if they include equivalent structural elements with insubstantial differences from the literal language of the claims.

What is claimed is:

1. A method of reducing one or both of total serum cholesterol and serum LDL cholesterol in a human subject, the method comprising administering atrasentan, or a pharmaceutically acceptable salt thereof, in an amount of from about 0.5 mg to about 5 mg to effect a reduction of about 5% or more in one or both of (a) total serum cholesterol, relative to a baseline total serum cholesterol of the subject, and (b) serum LDL cholesterol, relative to a baseline serum LDL cholesterol of the subject.

2. The method of claim 1, wherein a reduction is effected for both (a) total serum cholesterol, relative to a baseline total serum cholesterol of the subject, and (b) serum LDL cholesterol, relative to a baseline serum LDL cholesterol of the subject.

3. The method of claim 1, wherein a pharmaceutically acceptable salt of atrasentan is administered to the subject.

4. The method of claim 3, wherein the pharmaceutically acceptable salt administered to the subject is atrasentan hydrochloride.

5. The method of claim 1, wherein total serum cholesterol is reduced by about 10% or more, relative to the subject's baseline total serum cholesterol.

6. The method of claim 5, wherein the total serum cholesterol is reduced by about 15% or more, relative to the subject's baseline total serum cholesterol.

7. The method of claim 6, wherein the total serum cholesterol is reduced by about 20% or more, relative to the subject's baseline total serum cholesterol.

8. The method of claim 1, wherein the total serum cholesterol is reduced by about 10% to about 25%, relative to the subject's baseline total serum cholesterol.

9. The method of claim 8, wherein the total serum cholesterol is reduced by about 15% to about 25%, relative to the subject's baseline total serum cholesterol.

10. The method of claim 1, wherein serum LDL cholesterol is reduced by about 10% or more, relative to the subject's baseline serum LDL cholesterol.

11. The method of claim 10, wherein the serum LDL cholesterol is reduced by about 15% or more, relative to the subject's baseline serum LDL cholesterol.

12. The method of claim 11, wherein the serum LDL cholesterol is reduced by about 20% or more, relative to the subject's baseline serum LDL cholesterol.

13. The method of claim 10, wherein the serum LDL cholesterol is reduced by about 10% to about 25%, relative to the subject's baseline serum LDL cholesterol.

14. The method of claim 13, wherein the serum LDL cholesterol is reduced by about 15% to about 25%, relative to the subject's baseline serum LDL cholesterol.

15. The method of claim 1, wherein total serum cholesterol is reduced, relative to baseline, by about 10 mg/dL or more.

16. The method of claim 15, wherein total serum cholesterol is reduced, relative to baseline, by about 20 mg/dL or more.

17. The method of claim 15, wherein total serum cholesterol is reduced, relative to baseline, by about 10 mg/dL to about 25 mg/dL.

18. The method of claim 17, wherein total serum cholesterol is reduced, relative to baseline, by about 15 mg/dL to about 25 mg/dL.

19. The method of claim 1, wherein serum LDL cholesterol is reduced, relative to baseline, by about 10 mg/dL or more.

20. The method of claim 19, wherein serum LDL cholesterol is reduced, relative to baseline, by about 20 mg/dL or more.

21. The method of claim 19, wherein serum LDL cholesterol is reduced, relative to baseline, by about 10 mg/dL to about 25 mg/dL.

22. The method of claim 21, wherein serum LDL cholesterol is reduced, relative to baseline, by about 15 mg/dL to about 25 mg/dL.

23. The method of claim 1, wherein about 0.5 mg to about 1.5 mg atrasentan, or a pharmaceutically acceptable salt thereof, is administered to the subject.

24. The method of claim 23, wherein about 0.75 mg to about 1.25 mg atrasentan, or a pharmaceutically acceptable salt thereof, is administered to the subject.

25. The method of claim 24, wherein about 0.75 mg atrasentan, or a pharmaceutically acceptable salt thereof, is administered to the subject.

26. The method of claim 1, wherein atrasentan, or a pharmaceutically acceptable salt thereof, is administered daily to the subject.

27. The method of claim 1, further comprising administering a therapeutically effective amount of a HMG-CoA reductase inhibitor to the subject.

28. The method of claim 27, further comprising administering a therapeutically effective amount of a statin to the subject.

29. The method of claim 1, wherein the subject is suffering from an illness selected from the group consisting of coronary heart disease, hypercholesterolemia, hyperlipidemia, nephropathy, chronic kidney disease, diabetes, and albuminuria.

30. The method of claim 29, wherein the subject is suffering from hypercholesterolemia.

31. The method of claim 29, wherein the subject is suffering from hyperlipidemia.

32. The method of claim 29, wherein the subject is suffering from diabetes.

33. The method of claim 32, wherein the subject is suffering from type 2 diabetes.

* * * * *